(12) United States Patent
Lin et al.

(10) Patent No.: US 11,311,215 B2
(45) Date of Patent: Apr. 26, 2022

(54) MEASUREMENT OF DEVICE MATERIALS USING NON-FARADAIC ELECTROCHEMICAL IMPEDANCE SPECTROSCOPY

(71) Applicant: MEDTRONIC MINIMED, INC., Northridge, CA (US)

(72) Inventors: Chi-En Lin, Van Nuys, CA (US); David Probst, Chandler, AZ (US); Mohsen Askarinya, Chandler, AZ (US); Akhil Srinivasan, Pacific Palisades, CA (US); Melissa Tsang, Sherman Oaks, CA (US); Michael E. Miller, Culver City, CA (US); Parisa Kamgar, Los Angeles, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 354 days.

(21) Appl. No.: 16/375,752

(22) Filed: Apr. 4, 2019

(65) Prior Publication Data
US 2020/0315504 A1  Oct. 8, 2020

(51) Int. Cl.
| | |
|---|---|
| *A61B 5/145* | (2006.01) |
| *A61B 5/1486* | (2006.01) |
| *G01N 27/327* | (2006.01) |
| *C12Q 1/54* | (2006.01) |
| *G01N 27/02* | (2006.01) |
| *A61B 5/00* | (2006.01) |
| *C12Q 1/00* | (2006.01) |

(52) U.S. Cl.
CPC ........ *A61B 5/14532* (2013.01); *A61B 5/0004* (2013.01); *A61B 5/1486* (2013.01); *C12Q 1/002* (2013.01); *C12Q 1/54* (2013.01); *G01N 27/026* (2013.01); *G01N 27/3271* (2013.01)

(58) Field of Classification Search
None
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Antwerp et al. |

(Continued)

*Primary Examiner* — J. Christopher Ball
(74) *Attorney, Agent, or Firm* — Gates & Cooper LLP

(57) ABSTRACT

The invention includes method and materials designed to measure the material properties (e.g. thickness) of layers of material in a sensor using non-Faradaic EIS (Electrochemical Impedance Spectroscopy) methods. The methods are non-destructive, very sensitive and rapid. Typically in these methods, an AC voltage is applied to the desired material layer while the output current and therefore impedance is measured. This voltage can be applied in multiple frequencies in sweep mode in order to detect both the material and, for example, the thickness of the target material. In this way, EIS allows the characterization of properties of various layers of material disposed in devices such as electrochemical glucose sensors.

18 Claims, 38 Drawing Sheets

SINUSOIDAL PERTURBATION APPLIED AND DIFFERENCE MEASURED

Signal applied to the system → Change in phase due to properties of system being affected

(56) References Cited

U.S. PATENT DOCUMENTS

| | | | |
|---|---|---|---|
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 2007/0123819 | A1 | 5/2007 | Mernoe et al. |
| 2010/0160861 | A1 | 6/2010 | Causey, III et al. |
| 2012/0006100 | A1* | 1/2012 | Gottlieb ............ A61B 5/742 73/53.01 |
| 2015/0164382 | A1* | 6/2015 | Varsavsky ........ G01N 27/026 600/347 |

\* cited by examiner

- EIS is an AC based measurement technique that applies an AC voltage, at an unique potential, and measures output impedance.
- Non destructive, Ultra-sensitive, rapid, labelfree, point-of-care method $$Z\,Total = Z'(real) + Z''(imaginary) = R_s + \frac{R_{ct}}{(1+(\omega C_{ct} R_{ct})^2)} + \frac{\omega C_{ct} R_{ct}^2}{(1+(\omega C_{ct} R_{ct})^2)}$$

- EIS can varies between different types of physics due the sensitivity, and nature of the platform.
- All materials have unique dielectrics, conductance, impedance, and capacitance behaviors that respond to various frequencies.
- Leveraging a sweeping frequency differential layers can be detected, both by material, and thickness of the material.

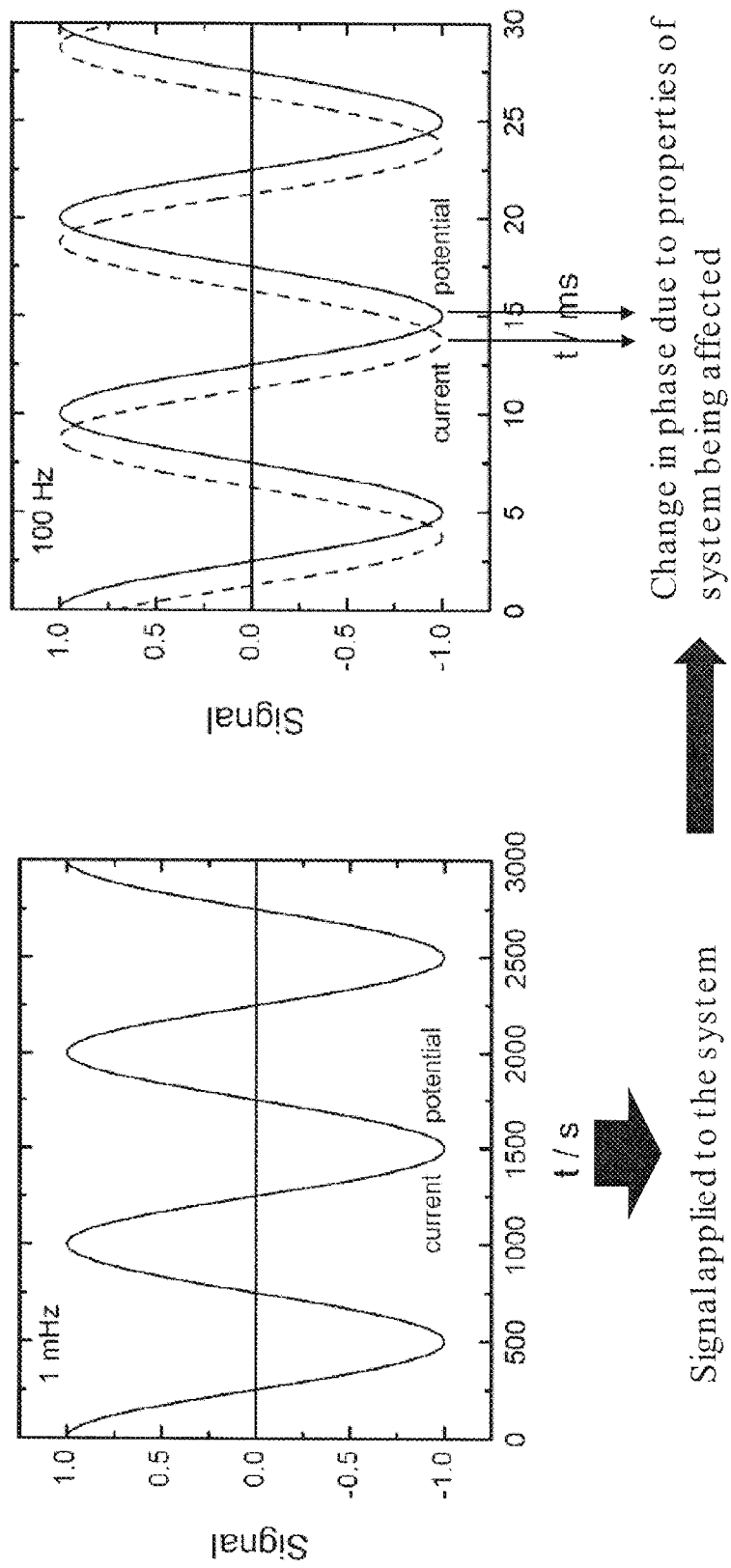

COMMON CIRCUITS APPLIED TO NYQUIST PLOTS

CIRCUIT COMPONENTS

When modeling circuit start with simple designs that can be translated into physical phenomena such as diffusion, surface coverage, electron kinetics, and transport properties

TRANSFER FUNCTION FOR BASIC RC CIRCUIT

Breaking down the circuit to transfer functions can allow for quantification of various electrical effects off a system being interrogated.

Note: $w = 2*PI*Frequency$

FIG. 2D
MODIFIED RANDEL'S CIRCUITS (CPE) ELEMENT

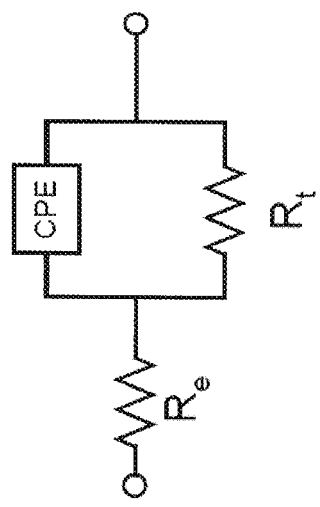

$$\frac{Z - R_e}{R_t} = \frac{1}{1 + (j\omega)^\alpha R_t Q}$$

Constant phase element is commonly used to better model data, has been described to represent various physics, ranging from imperfect capacitor to heterogeneous surface energy, electrode roughness, distribution of reaction rate constants, nonuniform current, coupled reactions and some claim this to be a simple fitting parameter with little to no physical meaning.

Be sure you have a physical reason to model data in various forms, do not fit data just because of a strong "fit".

FIG. 2E CPE CONTINUED
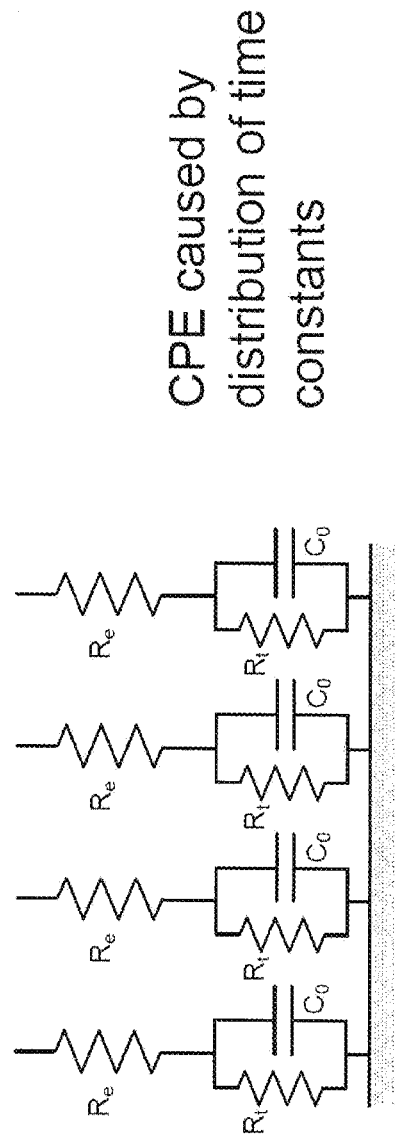
Semi-Circle
$$Z = R_e + \frac{R_t}{1 + j\omega C_0 R_t}$$
Depressed Semi-Circle
$$Z = R_e + \frac{R_t}{1 + (j\omega)^\alpha Q R_t}$$
CPE caused by distribution of time constants
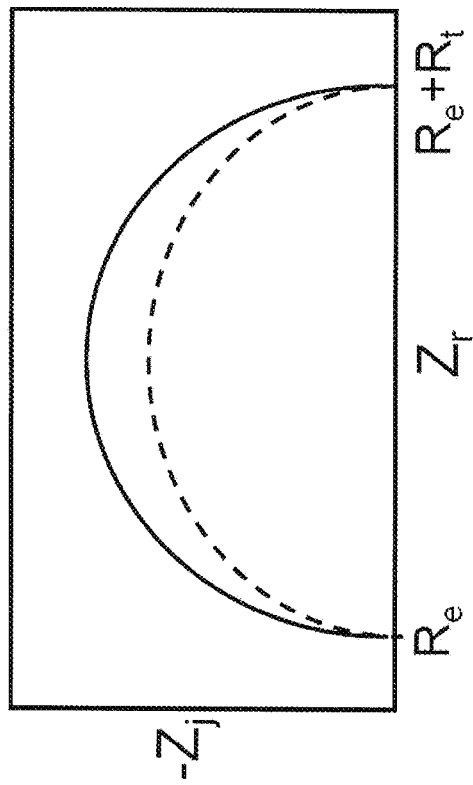

CIRCUIT EXAMPLES: BLOCKED ELECTRODE EXAMPLE $$Z = R_e + \frac{Z_F}{1 - \gamma + j\omega(\gamma C_\ell + (1-\gamma)C_{dl})Z_F}$$

The change in physical absorption should alter the Cl component of the circuit model. Note that no enzyme, or reaction is currently used in this system

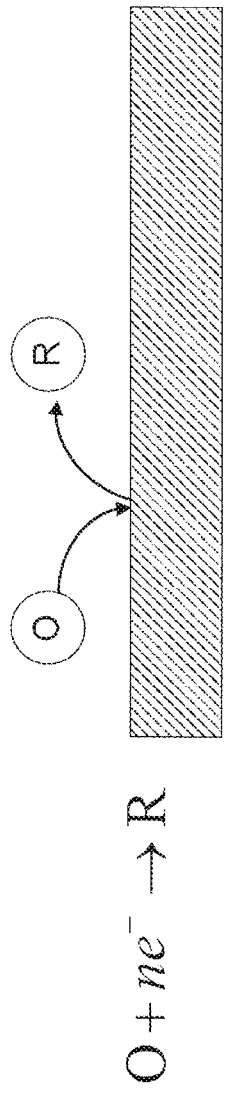

Current chemical layers deposited onto the E3 sensors are quality controlled through imaging, and destructive methods. These inspections are not 100% which leaves sensors unmonitored.

ELECTROCHEMICAL IMPEDANCE SPECTROSCOPY

- Developed a quality control process for individual chemical layer measurement using an electrolyte free EIS method (dry). Preliminary test have been performed on GLM, GOX, HSA vs HSA+GA+AP.

BASED ON PAPER "ANALYSIS OF THE PLANAR ELECTRODE MORPHOLOGY FOR CAPACITIVE CHEMICAL SENSORS"

EIS TEST PADS

- Currently working on a test board to measure EIS using various designs. Comparing which will return better SNR based on resistance, and capacitance of test board.

FINDING AN OPTIMAL FREQUENCY

INTERVAL PLOTS

INTERVAL PLOTS
- Day 1,
- Frequency: 100Hz-500Hz
- RealCapacitance
- Sensors Average

INTERVAL PLOTS
- Day 1,
- Frequency: 100Hz-500Hz
- Imaginary Capacitance
- Sensors Average

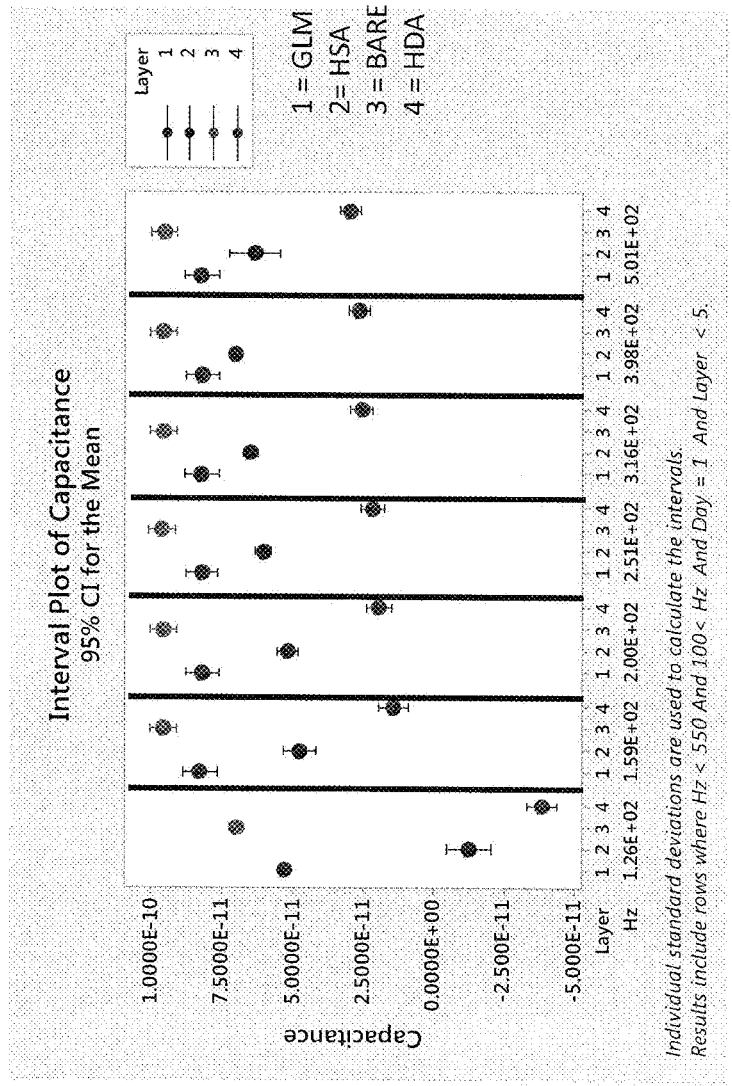

INTERVAL PLOTS

- Day 1,
- Frequency: 100Hz-500Hz
- Sensors Average
- w=conductance/capacitance

INTERVAL PLOTS
- Day 1,
- Frequency: 150Hz-500Hz
- Complex Z
- Sensors Average

INTERVAL PLOTS
- Day 1,
- Frequency: 100Hz-500Hz
- Sensors Average
- conductance

INTERVAL PLOTS

- Day 1,
- Frequency: 250Hz–1000Hz,
- Sensors Average
- conductance

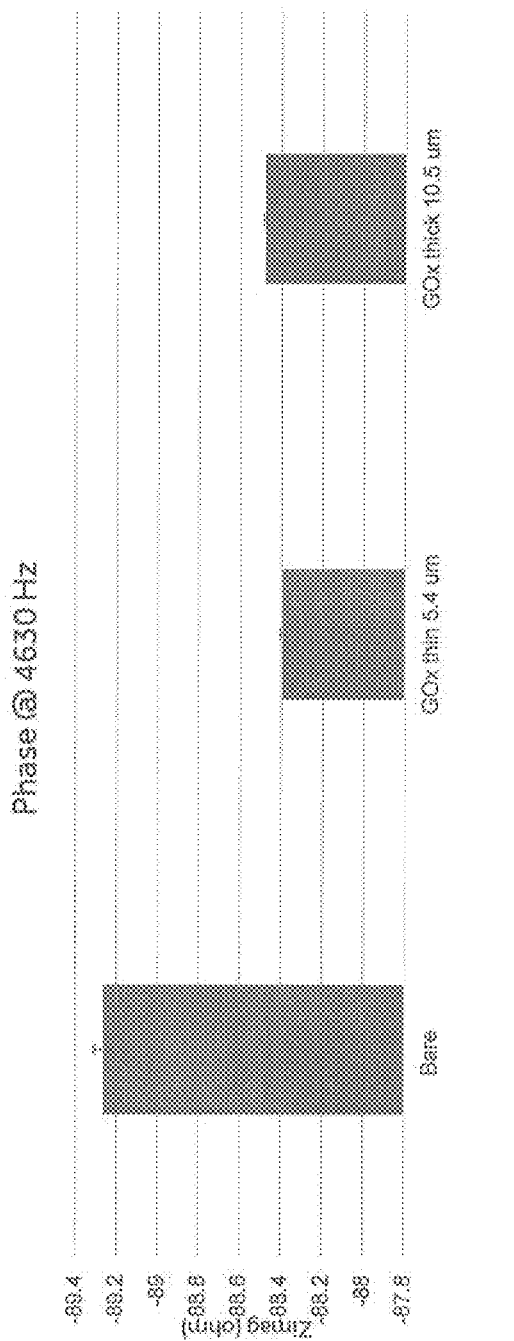

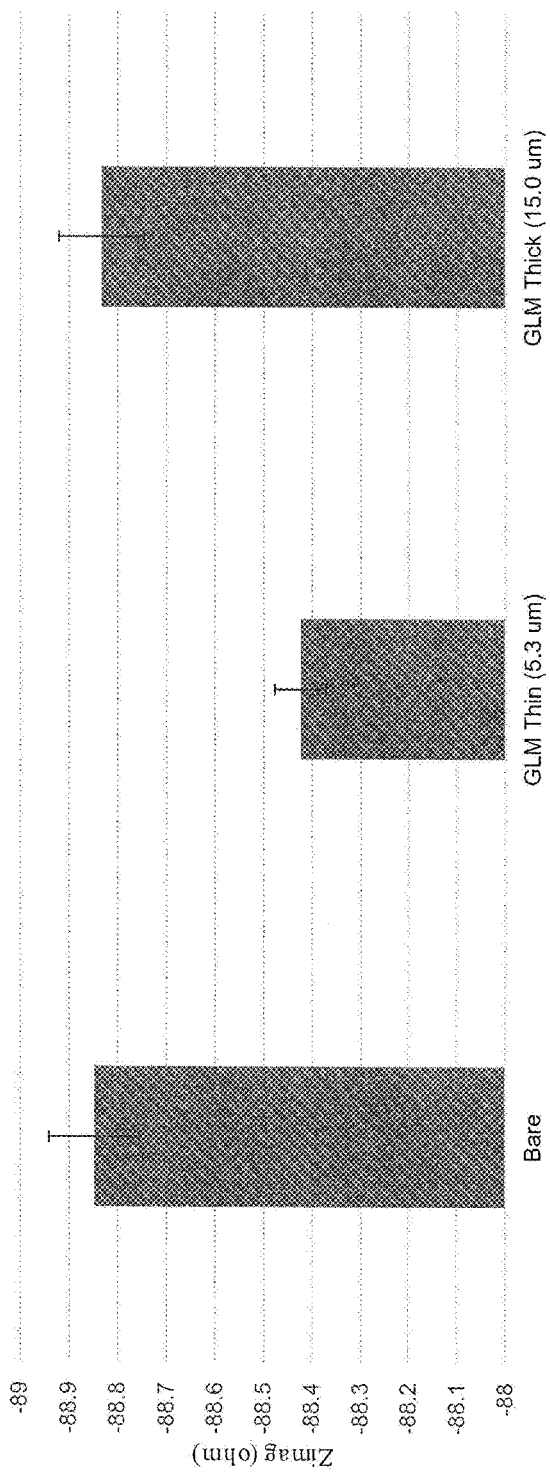

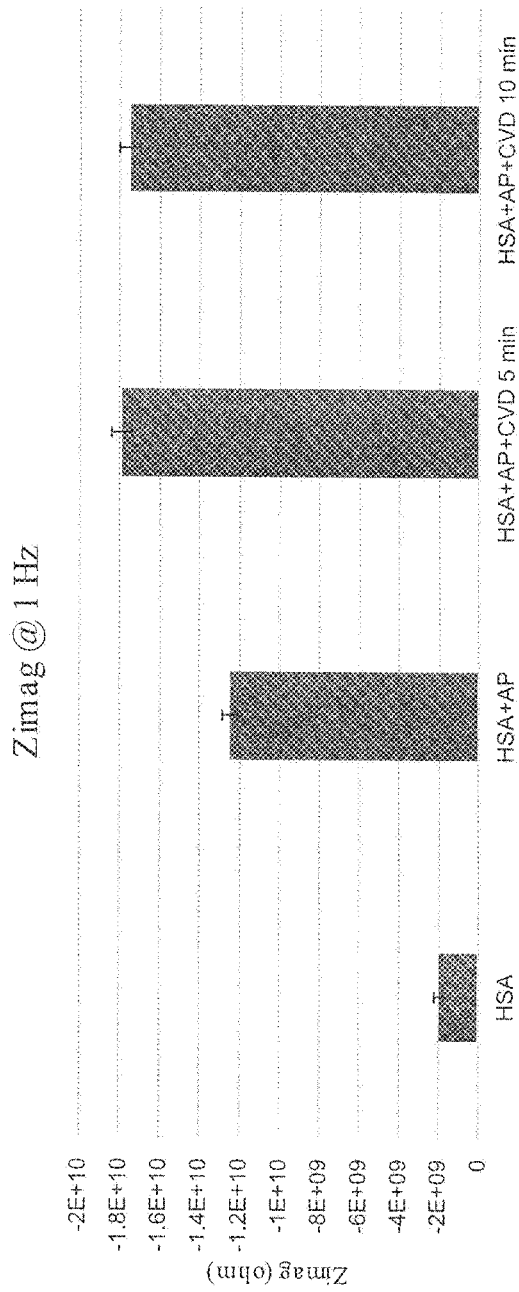

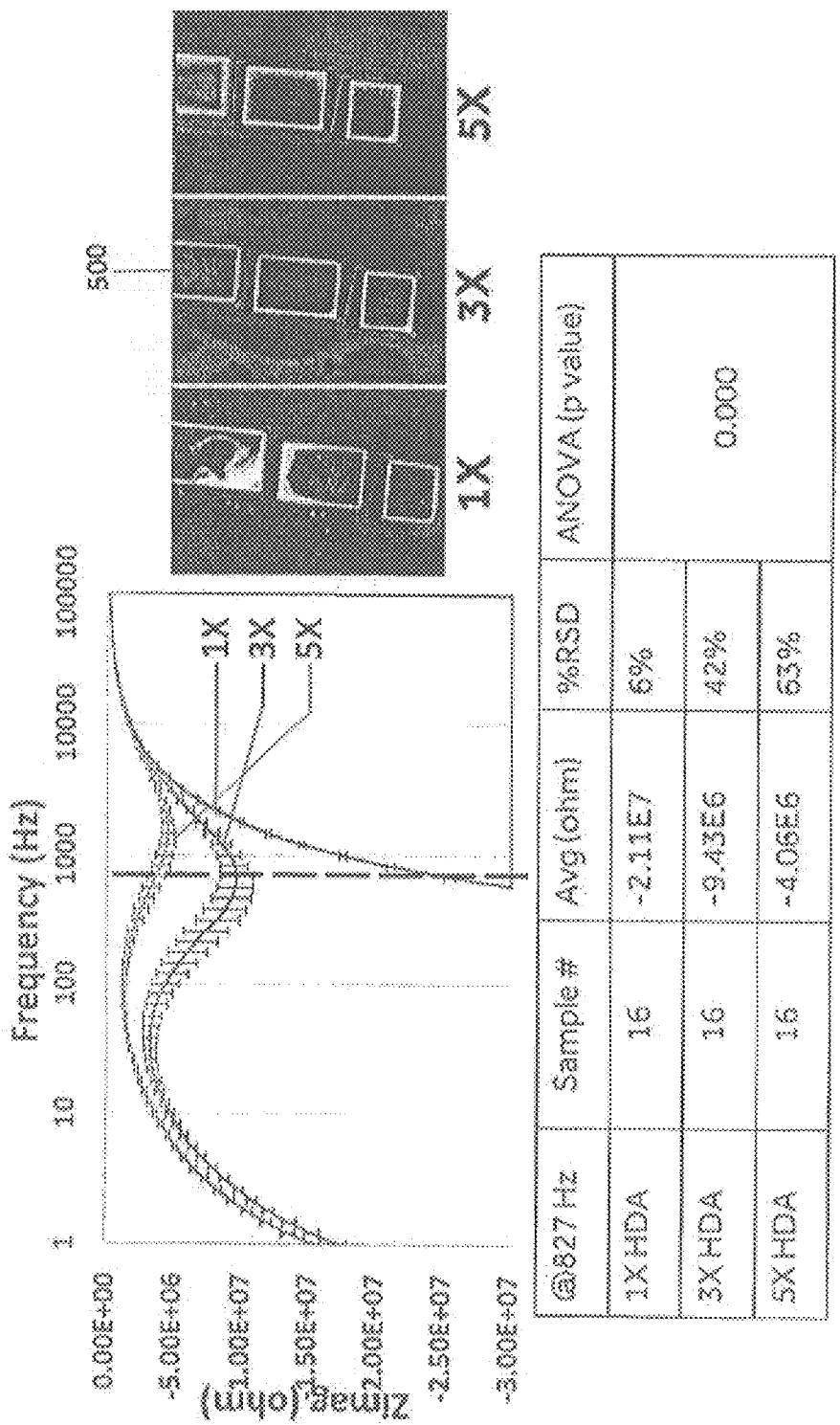

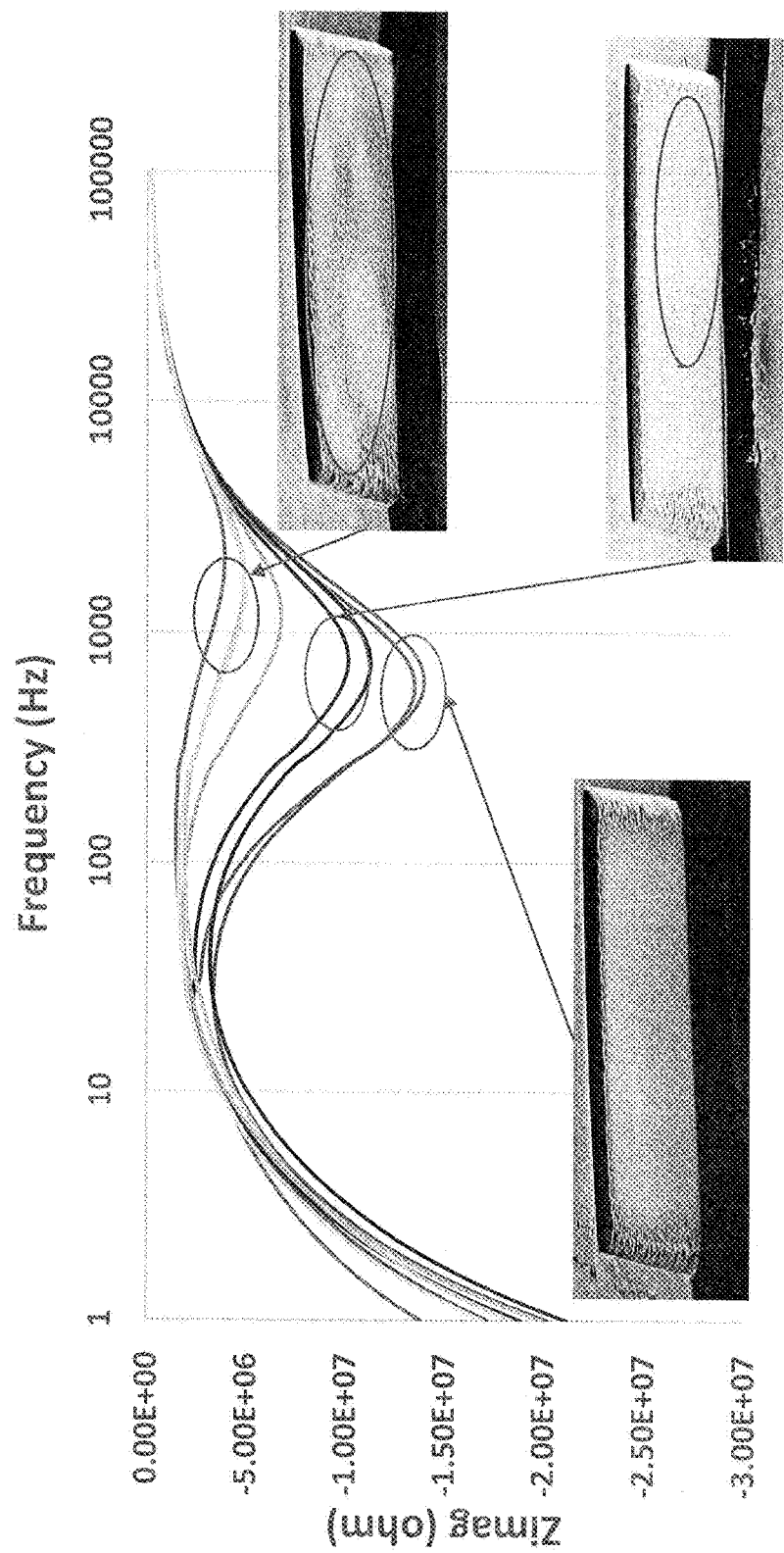

CORRELATION BETWEEN DRY EIS AND HUMIDITY TRACKS WELL AFTER EQUILIBRIUM IS REACHED

- EIS tracks well with humidity fluctuation with no lag time — until humidity drops below ~33% RH

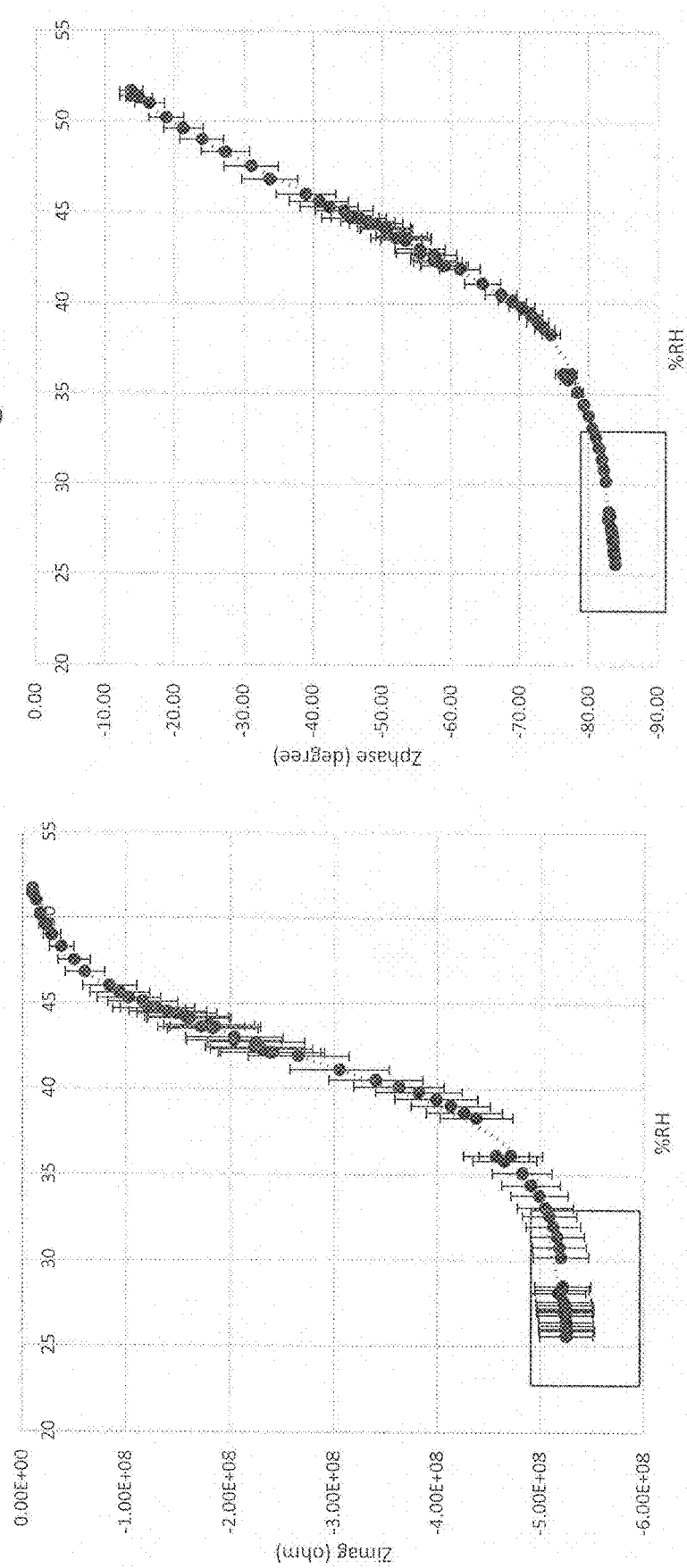

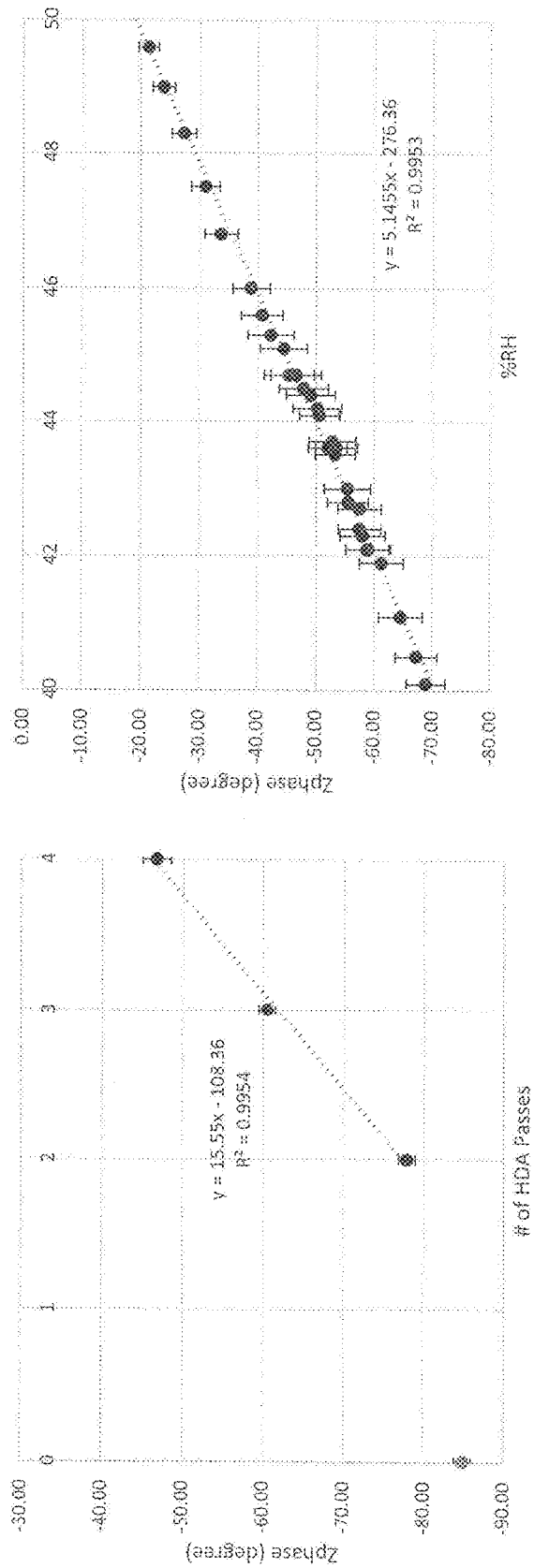

FIG. 8D
IMPACT OF HUMIDITY ON HDA
EXTREMELY SENSITIVE
Different Amounts of HDA

- $\dfrac{5.14 \frac{phase}{\%RH}}{15.55 \frac{phase}{[HDA]}} = 0.331 \dfrac{[HDA]}{\%RH}$ (call this the humidity robustness index)
- This means for every %RH variability during measurement, the dry EIS's prediction about # of HDA pass will be affected by 0.331.
- In other words, a 3% RH change will cause dry EIS to over/under estimate the # of HDA by 1

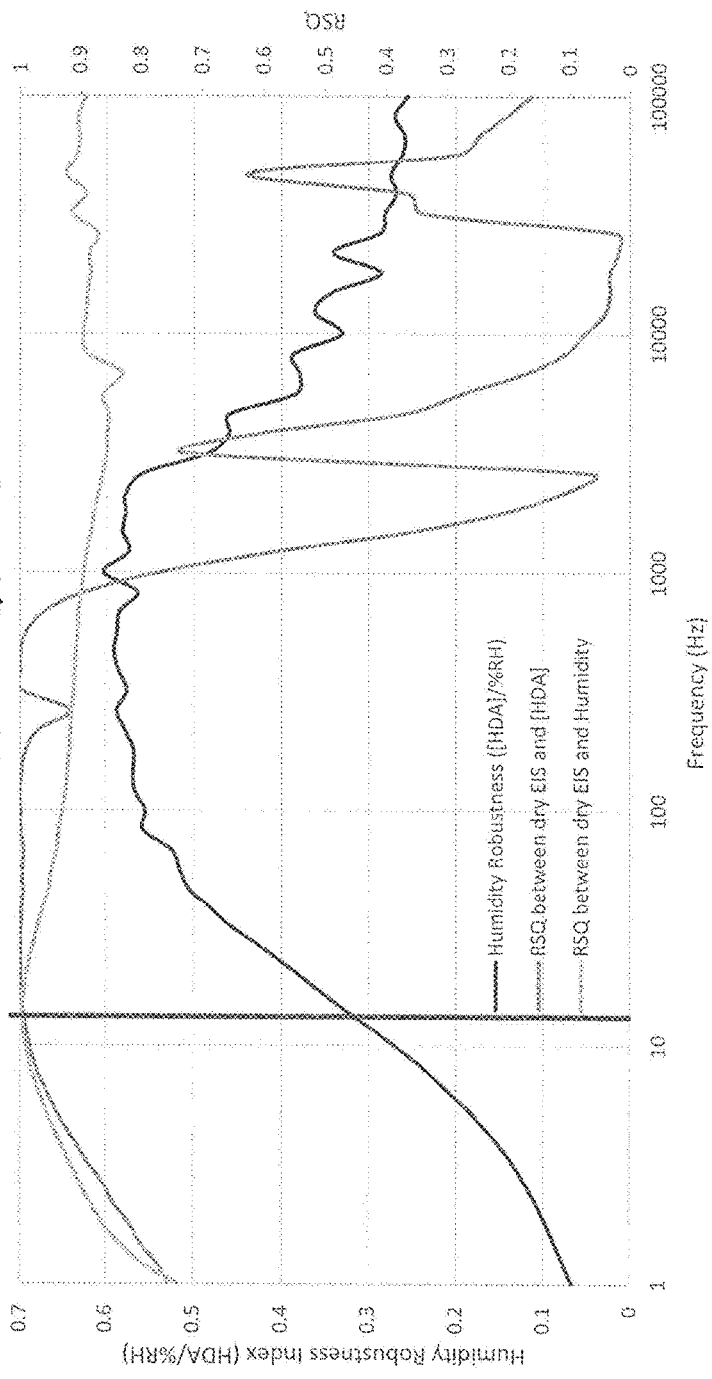

FIG. 8E
HUMIDITY SENSITIVITY ACROSS FREQUENCY

- First, looking at the orange trend, we want to pick a frequency that has great correlation (RSQ~0.99) between dry EIS signal and different amounts of HDA
  - That means we can work with 10 Hz to 100 Hz.
- However, looking at the blue curve, the dry EIS becomes more sensitive to humidity from 10 Hz to 100 Hz.
- Therefore we want something that's close to 10 Hz
- But either way, looking at the grey curve, EIS signal is sensitive to humidity regardless of frequency
  - Use 14.65 Hz with humidity input to control impedance output.

MEASUREMENT OF DEVICE MATERIALS USING NON-FARADAIC ELECTROCHEMICAL IMPEDANCE SPECTROSCOPY

TECHNICAL FIELD

The invention relates to the use of electrical impedance spectroscopy to assess device parameters and/or material characteristics.

BACKGROUND OF THE INVENTION

Subjects/patients and medical personnel wish to monitor readings of physiological conditions within the subject's body. Illustratively, subjects wish to monitor blood glucose levels in a subject's body on a continuing basis. Presently, a patient can measure his/her blood glucose (BG) using a BG measurement device (i.e. glucose meter), such as a test strip meter, a continuous glucose measurement system (or a continuous glucose monitor), or a hospital hemacue. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device.

Biomolecule sensors such as continuous glucose monitoring (CGM) sensors include enzyme based electrochemical biosensors that consist of multiple electrochemical electrodes which measure a chemical substrate via relation of electricity and chemical change. In typical CGM sensors, each glucose sensor consists of various layers, with electrodes on one layer which provide the interchange between patient and sensor. In such sensors, each layer has defined properties such as a target thickness for optimal functioning. Currently a reliable and effective method to measure properties such as the thickness of these material layers does not exist. By measuring properties such as the thickness of each layer on electrodes in devices such as CGM sensors, the properties of such devices can be observed during manufacturing processes.

There is a need in the field for additional methods and materials that allow artisans to assess device parameters and/or characteristics.

SUMMARY OF THE INVENTION

The invention disclosed herein provides method and materials designed to observe the properties of layers of material in devices such as electrochemical analyte sensors using non-Faradaic Electrochemical Impedance Spectroscopy (EIS). Typically, in these methods, an AC voltage is applied to the desired material layer while the output current and therefore impedance is measured. This voltage can be applied in multiple frequencies in sweep mode in order to detect both the material and, for example, the thickness, composition or architecture of the target material. In this way, EIS allows the characterization of various properties of material layers found in devices such as amperometric glucose sensors in a non-destructive, sensitive and rapid manner.

Traditionally, electrochemistry, such as Electrochemical Impedance Spectroscopy (EIS), is performed in solution, with the diffusion of ions in solution facilitating electron transferring mechanisms. Such electron transferring mechanisms result in EIS signals that are dependent on the material's properties of a surface being tested, and in this way provide useful information on the sample/material being examined by such methods. However, in the absence of a solution, ion diffusion does not occur, and the EIS signal resembles open circuit, a situation which typically provides little information regarding a sample/material. As discussed in detail below, we have discovered that when a material being examined by such methods has sufficient electron mobility; and the overall electrochemical cell has sufficient surface capacitance, electron transfer can occur via electron hopping amongst charged materials in a sample/material (e.g. polymers) in the absence of fluid, a phenomena which can yield EIS signals useful to observe or extrapolate sample/material properties. We have harnessed this discovery to generate embodiments of the invention, termed "dry" EIS, methodologies which can be used as a dry electrical test to evaluate material properties in MEMS fabrication, thereby avoiding the traditional use of fluids (and their associated complications) in MEMS fabrication The invention disclosed herein has a number of embodiments. Embodiments of the invention include methods of observing a property of a layer of a material disposed in a device comprising a first electrode electronically coupled to second electrode where the material layer is disposed over the first electrode and the second electrode. These methods comprise applying a voltage potential to the first electrode in a frequency sweep mode; and then measuring an output current that results from the application of the voltage potential. The methods then comprise using the measured output current to observe impedance characteristics of the material layer disposed over the first electrode and the second electrode; and then correlating the impedance characteristics with the property of the layer of material. The methods can be used to observe a variety of different properties of layer(s) of a material disposed in an electrochemical analyte sensor including, for example, the thickness of the material layer, the architecture or roughness of the material layer, the conductivity of the material layer, the concentration of one or more components in a composition that forms the material layer, or the homogeneity of a composition that forms the material layer. Advantageously, embodiments of the current method are quite rapid, and for example, take just 20 minutes to measure material layer thickness.

Embodiments of the invention allow for the indirect measurement of material properties of compositions (e.g. material layer thickness) in devices such as electrochemical glucose sensors during manufacturing processes. In these methods, a fixed AC voltage is applied to the contact point (e.g. a designated test pad for such test, aka PCM) while the impedance is being measured, and this voltage is applied in frequency sweep mode to capture different behaviors of the material in different frequencies. By applying a specific mathematical or other model of the measured impedance, specific material properties such as material thickness can be estimated.

Embodiments of the invention can be used to monitor manufacturing processes and provide valuable data about process variability and sensor to sensor variability. In particular, minute differences in process variability cause slight shifts in performance making calibration of the sensor difficult and increasing sensor to sensor performance variability. In addition, data from the EIS methodologies disclosed herein can be used as an input to algorithms to enable manufacturing calibration thereby overcoming difficulties in sensor calibration, sensor to sensor variability, and the like.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIGS. 1A-1D show schematics of Electrochemical Impedance Spectroscopy phenomena and techniques useful in practicing embodiments of the invention. FIG. 1A shows a schematic of EIS interrogation of an electrochemical cell. FIG. 1B shows a schematic of EIS data during interrogation of an electrochemical cell. FIG. 1C shows a schematic of EIS data and transform functions observed from such data. The left panel of FIG. 1C shows a graph of imaginary impedance versus real impedance, while the right panel shows transform functions observed from such data. FIG. 1D shows graphed data of a sinusoidal current potential signal applied to a system (left panel) and graphed data of changes of sinusoidal current potential from a signal applied to a system (right panel).

FIGS. 2A-2G shows common circuits useful in embodiments of the invention and associated illustrative interpretation of data form these circuits. FIG. 2A shows common circuits applied to Nyquist plots. FIG. 2B shows illustrative circuit components (top panel) and data obtained from such circuits (bottom panel). FIG. 2C shows transfer functions for basic RC circuitry. FIGS. 2D and 2E show modified Randel's circuit (CPE) elements (FIG. 2D) and data and circuits useful in such contexts (FIG. 2E). FIG. 2F shows circuit examples including a blocked electrode example circuit. FIG. 2G shows a schematic of faradaic current on a two-dimensional surface.

FIG. 3A shows schematics of illustrative sensor component layers (left panel) and illustrative sensor electrochemical structures and reactions (right panel). FIG. 3B shows schematics of EIS and sensor components performed in the presence of a liquid (left panel) and the absence of a liquid (right panel, "dry"). FIG. 3C shows the morphology of different electrode structures useful in embodiments of the invention. FIG. 3D shows the morphology of different electrode structures useful in embodiments of the invention.

FIGS. 4A-4I shows plots of data obtained from different material layers in a glucose sensor. FIG. 4A shows an interaction plot for phase data useful for finding an optimal frequency for observing various sensor layers. FIG. 4B shows a phase interval plot for observing various sensor layers. FIG. 4C shows a real capacitance interval plot for observing various sensor layers. FIG. 4D shows an imaginary capacitance interval plot for observing various sensor layers. FIG. 4E shows a capacitance interval plot for observing various sensor layers. FIG. 4F shows a complex impedance interval plot for observing various sensor layers. FIG. 4G shows a capacitance interval plot for observing various sensor layers. FIG. 4H shows a conductance interval plot for observing various sensor layers. FIG. 4I shows a conductance interval plot for observing various sensor layers.

FIGS. 5A-5G shows plots of data obtained from using embodiments of the invention to observe different material layers in a glucose sensor. FIG. 5A shows a plot of data from glucose oxidase material layers. FIG. 5B shows a plot of data from glucose limiting membrane material layers. FIG. 5C shows a plot of data from human serum albumin (HSA) material layers and human serum albumin in combination with adhesion promoting (AP) material layers. FIG. 5D shows a plot of data from 1, 3 or 5 coatings of high-density amine (HDA) material layers (left panel) and sensor elements coated with these layers (right panel). FIG. 5E shows a plot of data from 2×, 3× or 4× coatings of high-density amine (HDA) material layers. FIG. 5F shows a plot of data from coatings of high-density amine (HDA) material and images of the sensor elements tested. FIG. 5G shows a plot of data correlating EIS to material layer thickness.

FIGS. 8A-8E provide data from illustrative embodiments of the invention. FIG. 8A provides EIS Zimag (left panel) and Zphase (right panel) data showing a correlation between dry EIS and humidity that tracks well after equilibrium is reached until humidity drops below ~33% RH. FIG. 8B provides EIS Zimag (left panel) and Zphase (right panel) data showing a correlation between dry EIS and humidity that tracks well until ~33% RH, where the signal is equivalent to an open circuit. FIG. 8C provides EIS Zimag (left panel) and Zphase (right panel) data showing a correlation between dry EIS and humidity, with linearity occurring between 40%-50% RH, and an optimal frequency at Zphase that has higher linearity than that of Zimag. FIG. 8D provides EIS Zphase data with different HDA layers (left and right panels) data showing a correlation between dry EIS and humidity. FIG. 8E provides EIS data showing humidity sensitivity across varying frequencies (Hz) and that dry EIS becomes more sensitive to humidity from 10 Hz to 100 Hz.

DETAILED DESCRIPTION OF THE INVENTION

Figure 1A:
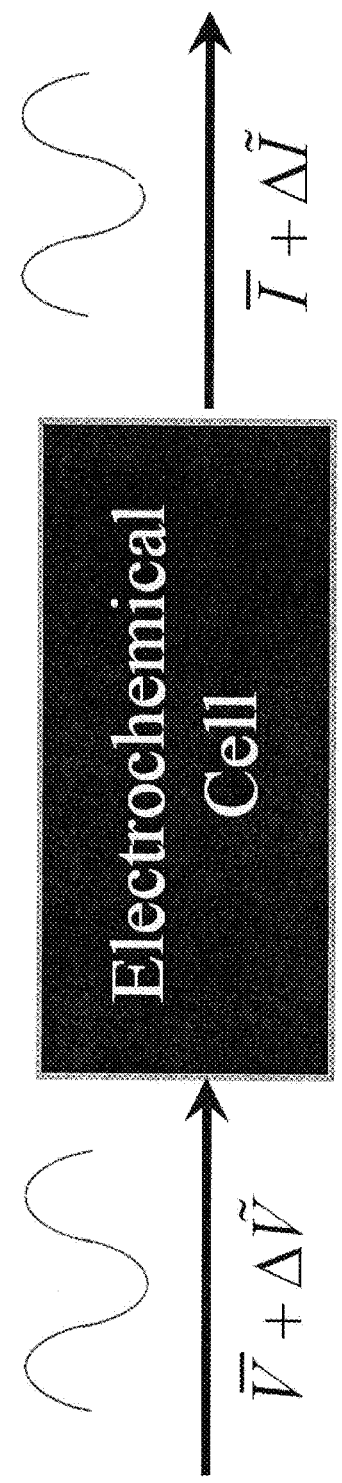
Figure 1B:
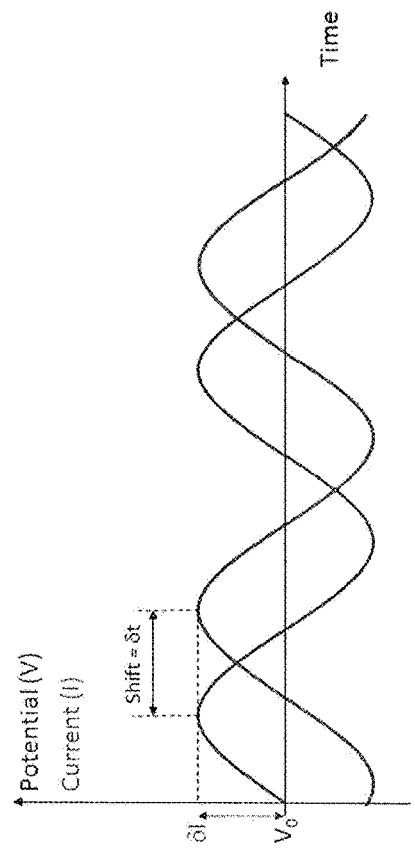
Figure 1C:
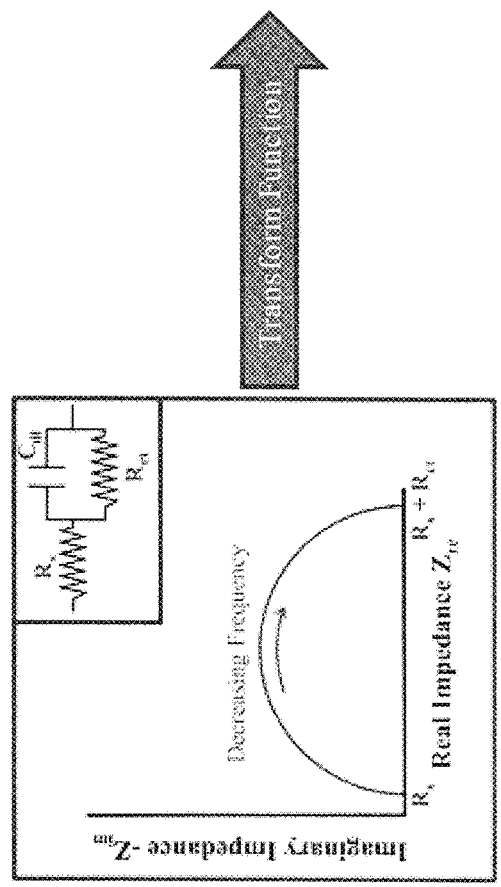
Figure 2A:
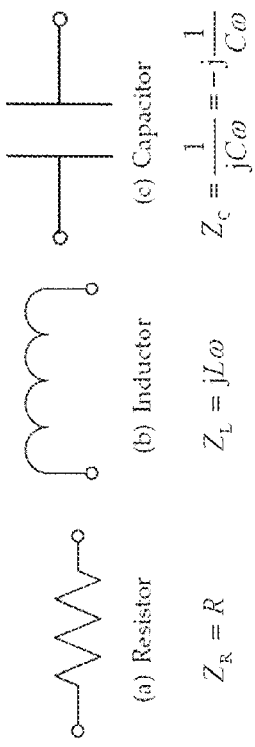
Figure 2A:
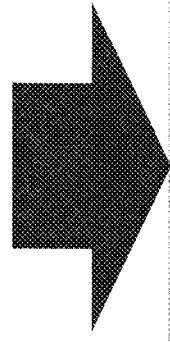
Figure 2A:
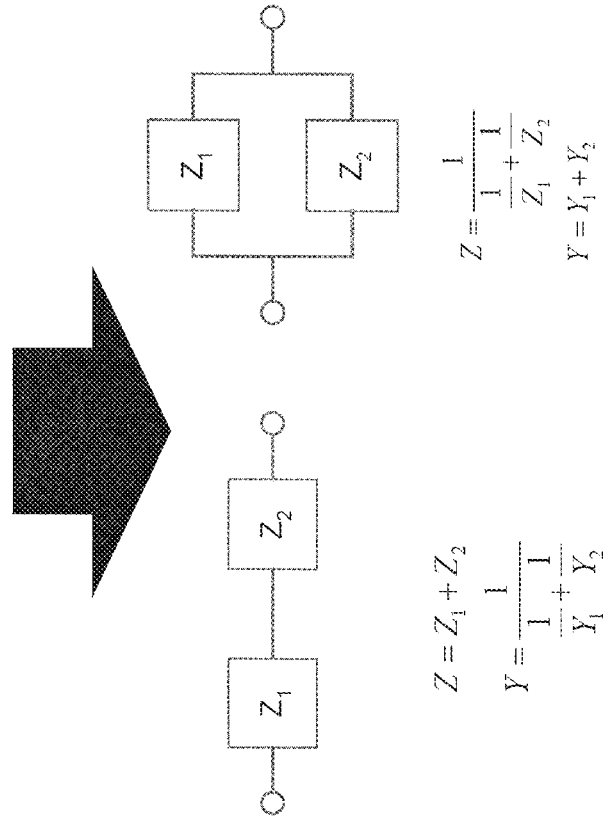
Figure 2B:
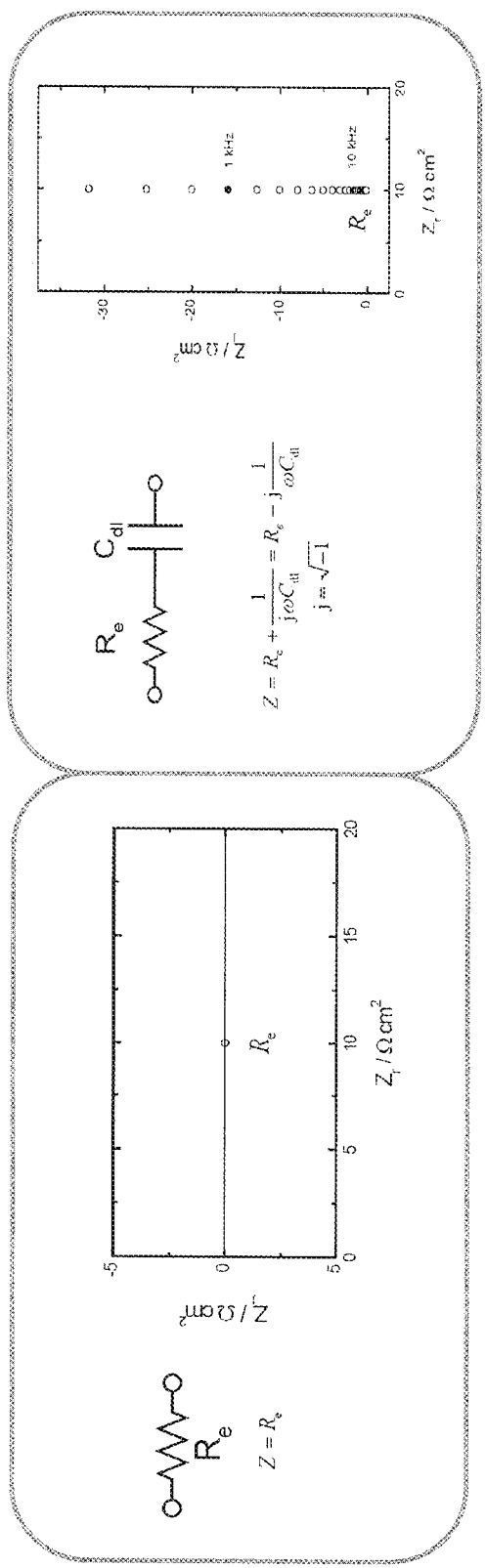
Figure 2B:
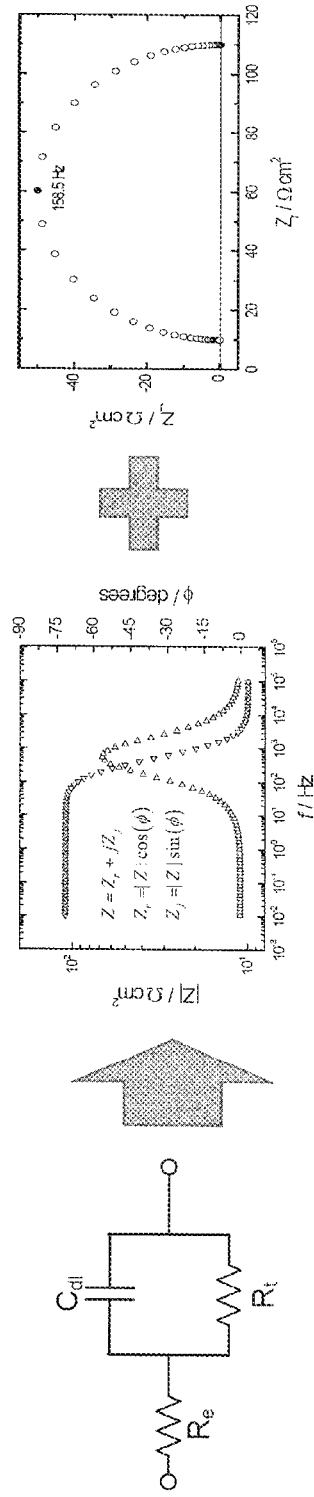
Figure 2C:
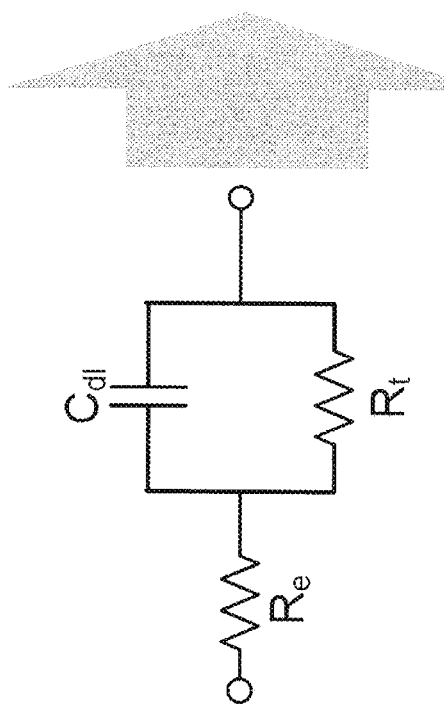
Figure 2F:
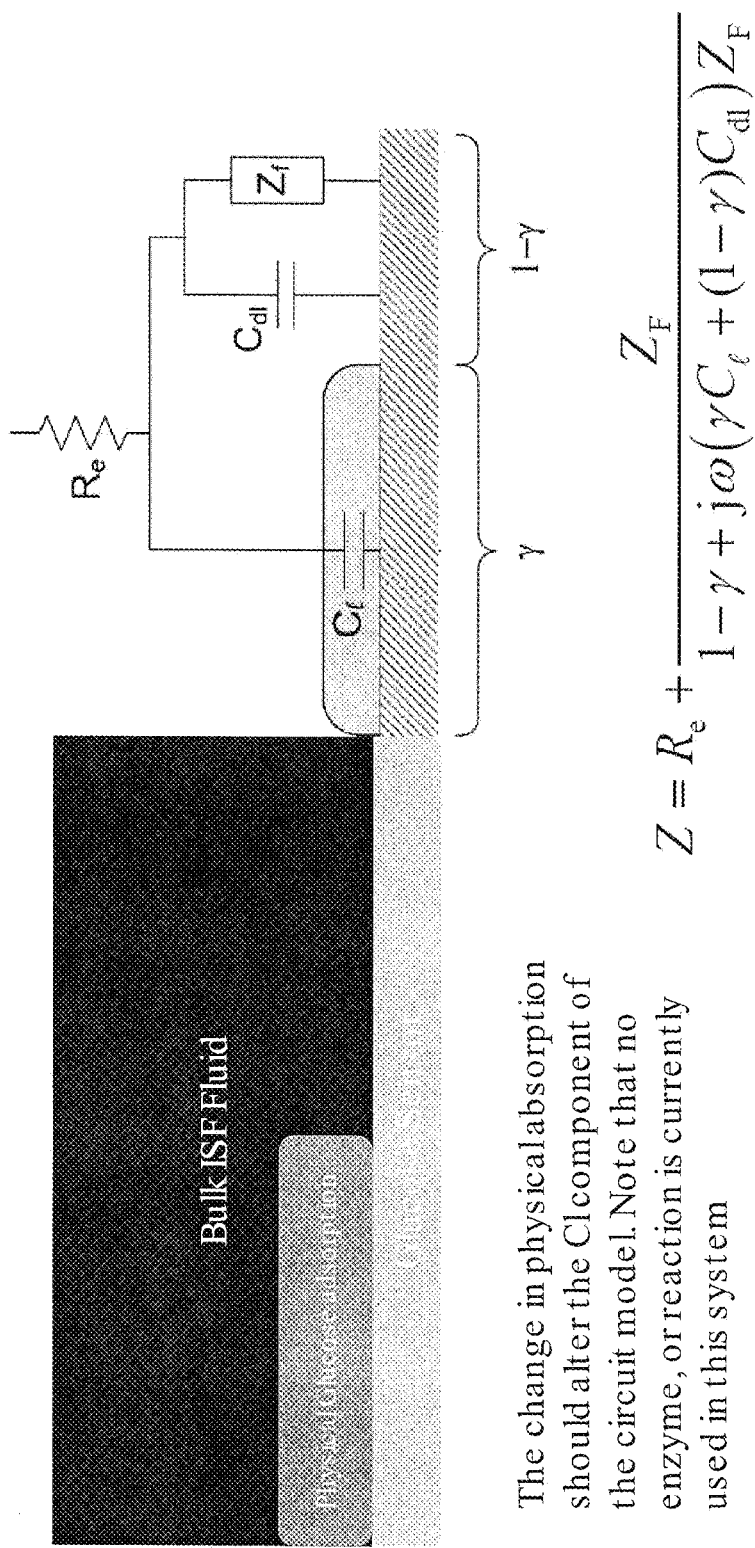
Figure 3A:
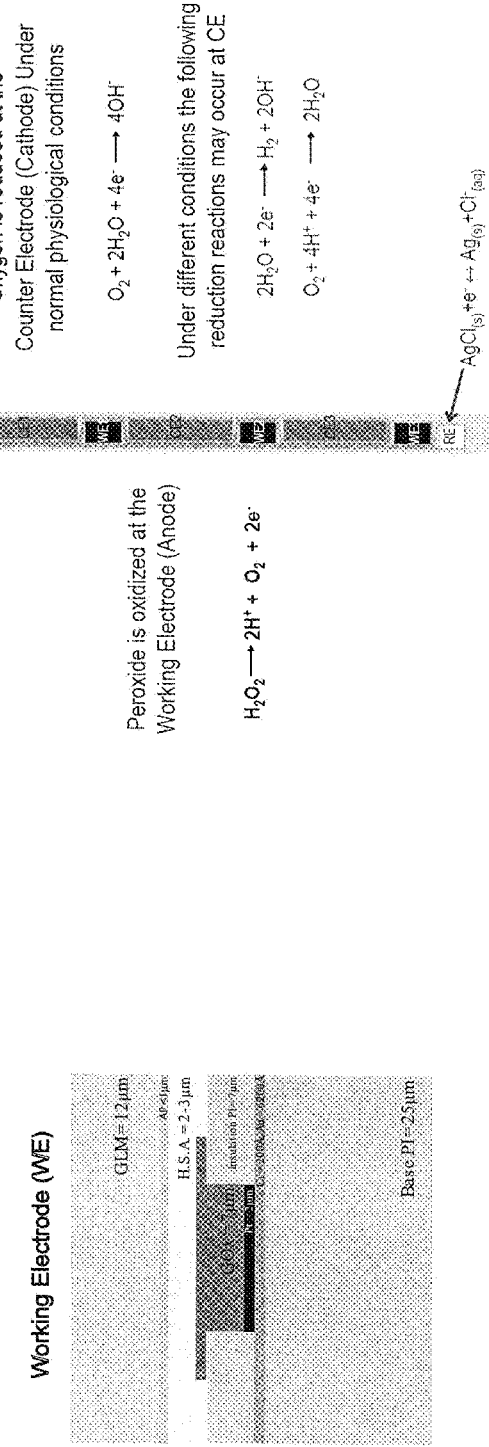
FIGS. 3A-3D shows the structures of sensor embodiments useful in embodiments of the invention.
Figure 3B:
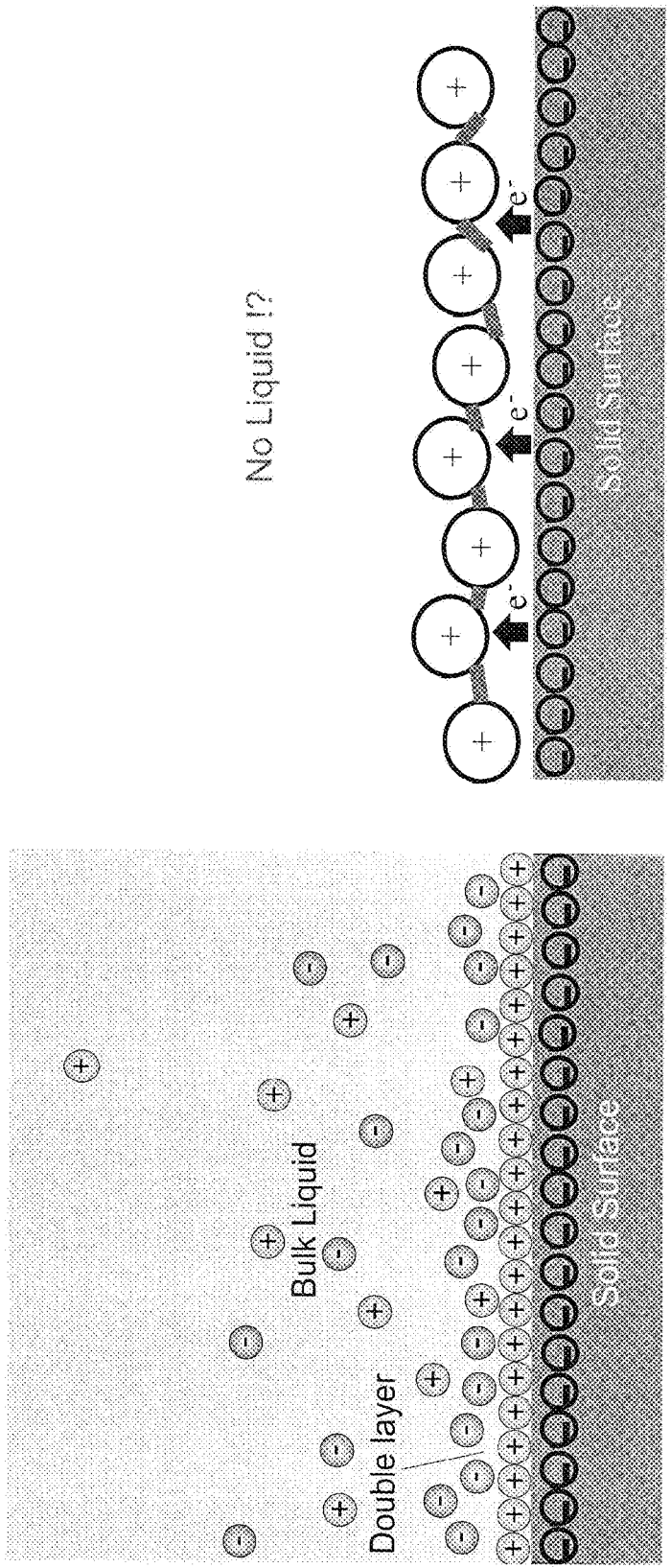
Figure 3C:
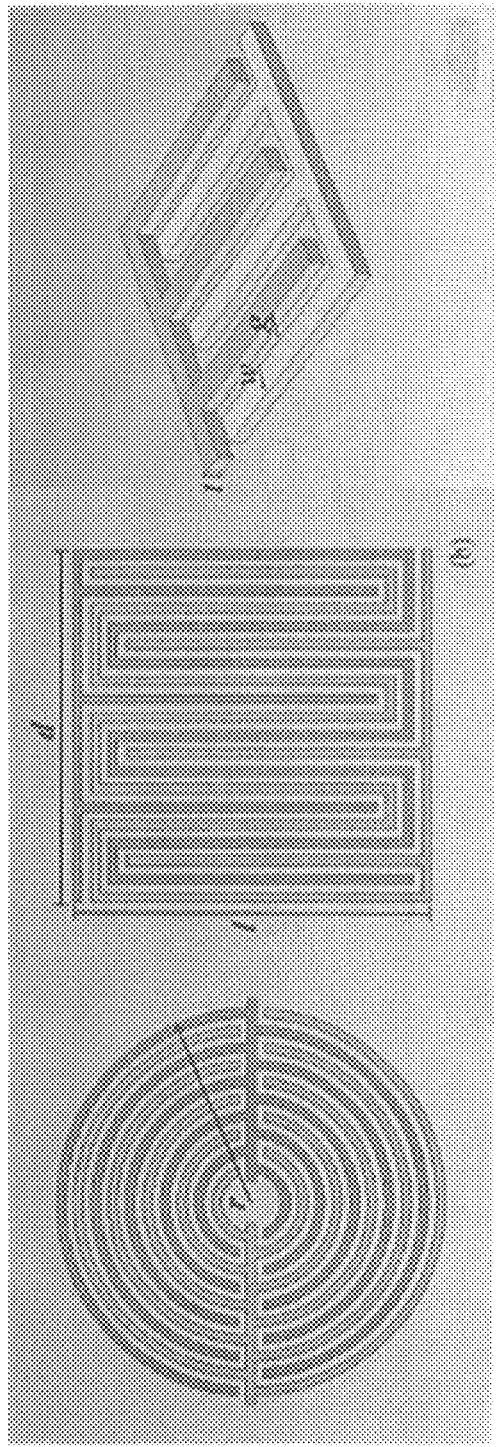
Figure 3D:
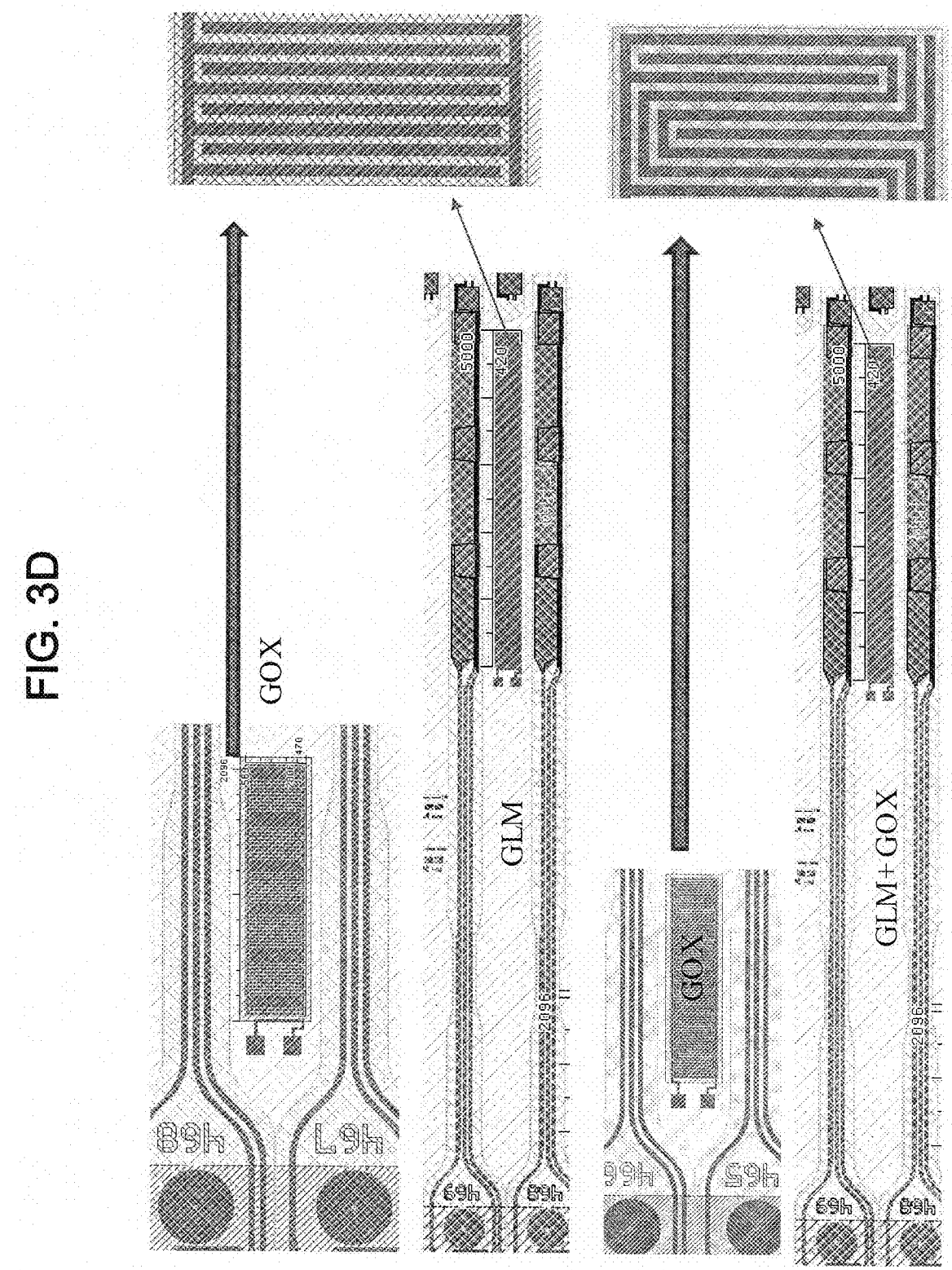
Figure 4A:
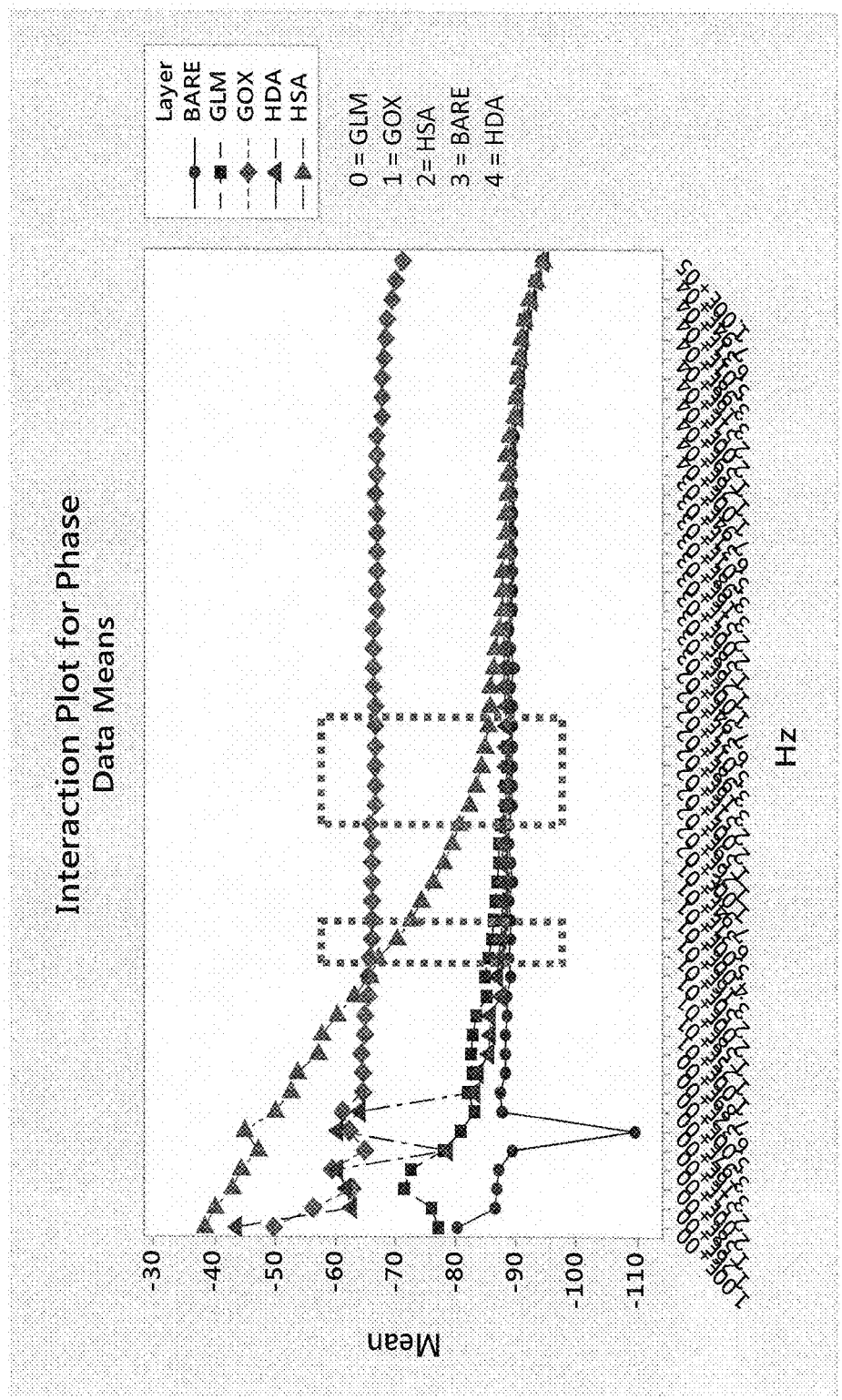
Figure 4B:
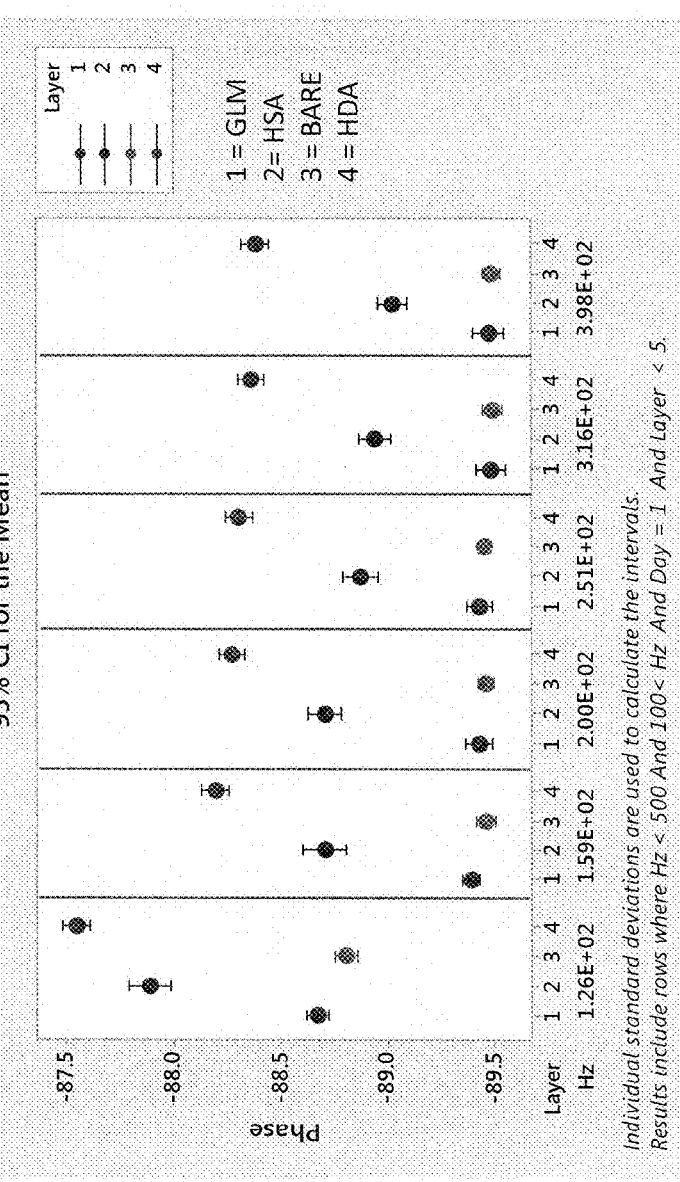
Figure 4C:
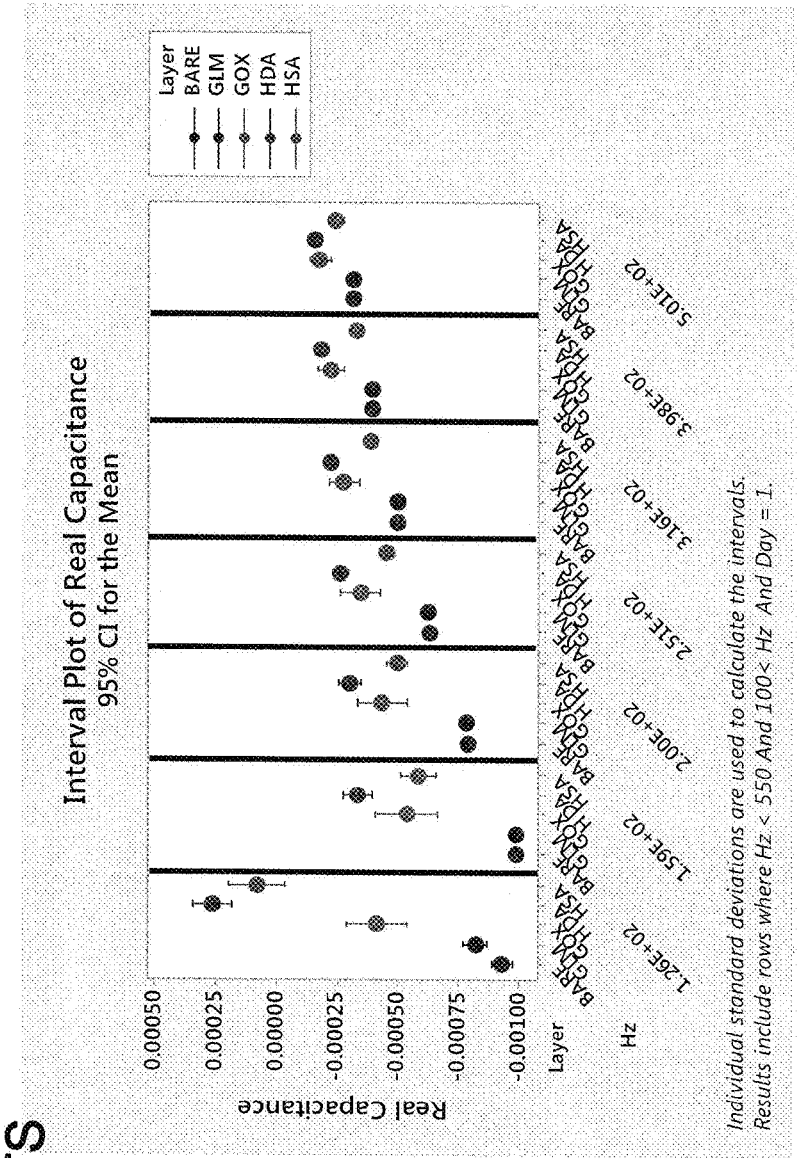
Figure 4D:
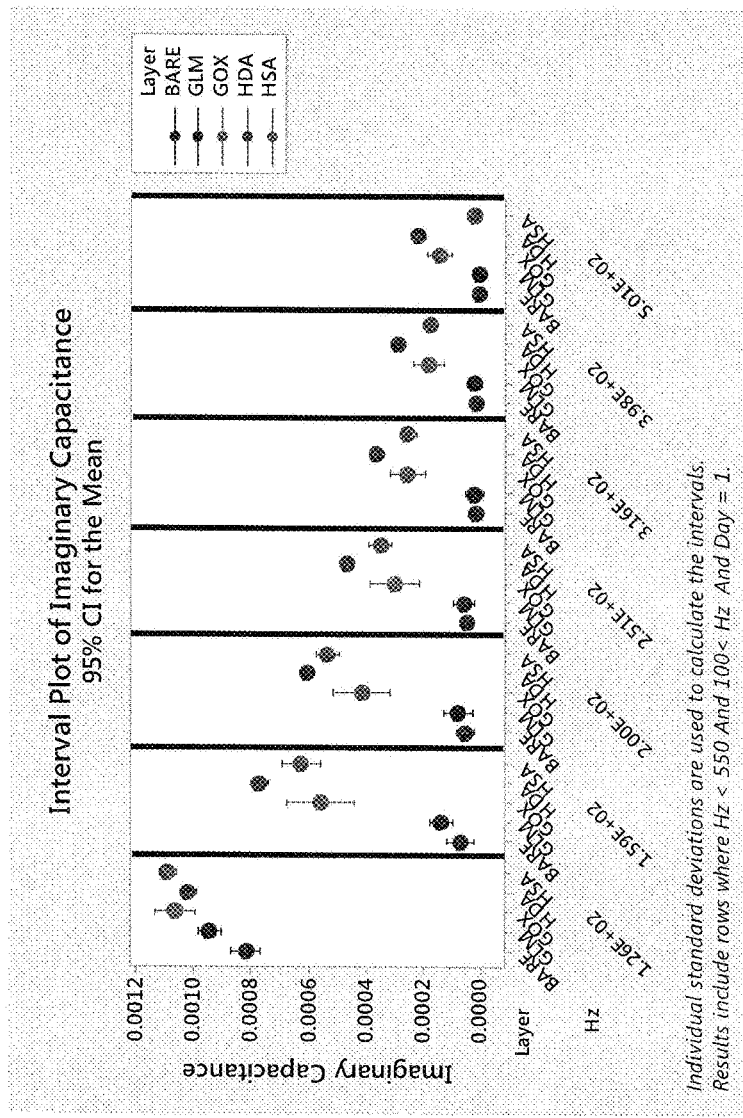
Figure 4F:
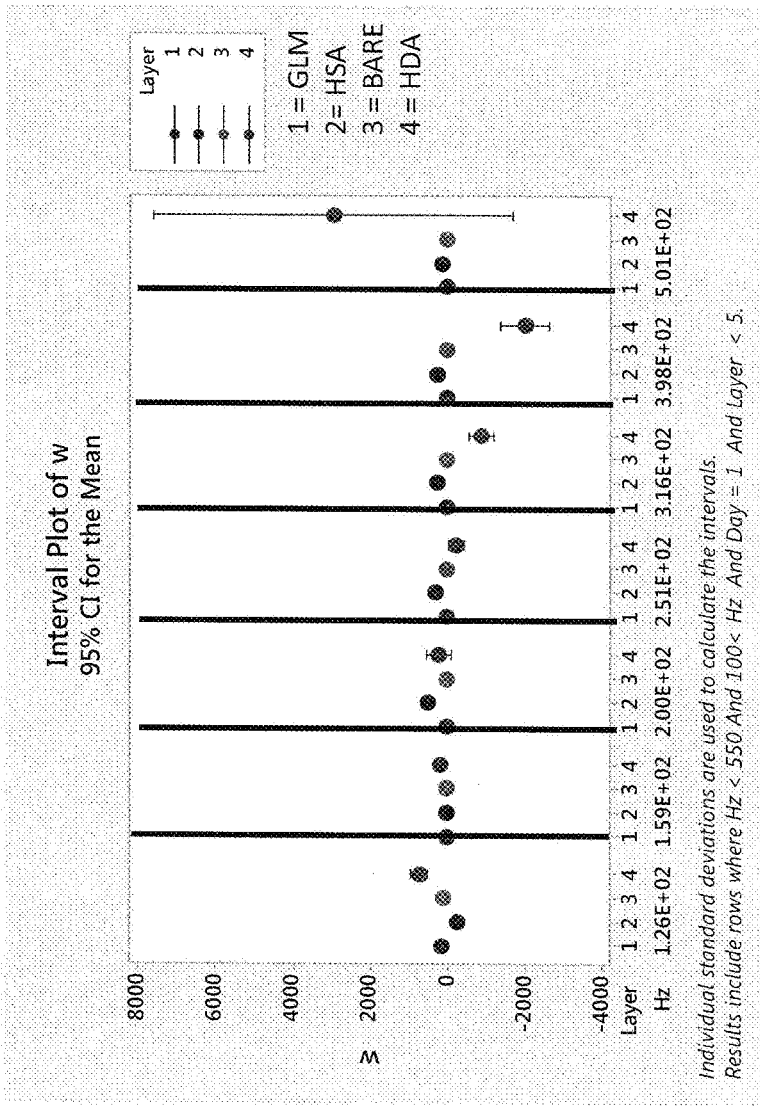
Figure 4G:
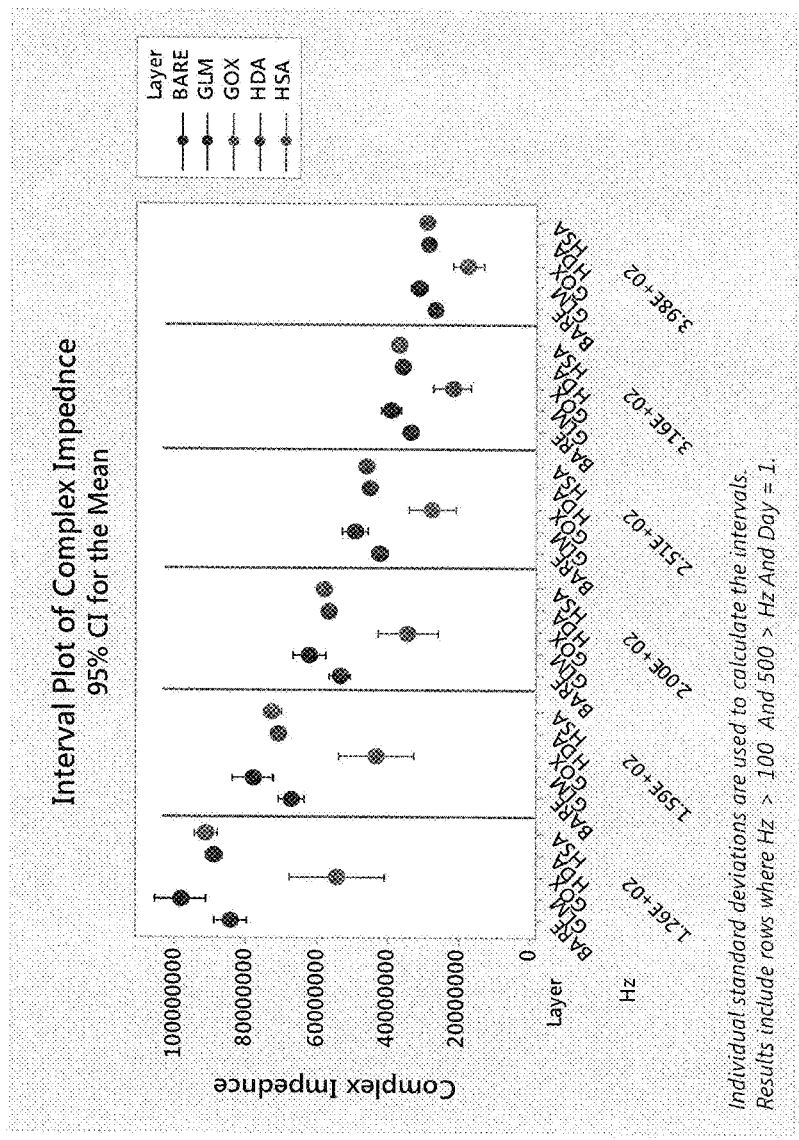
Figure 4H:
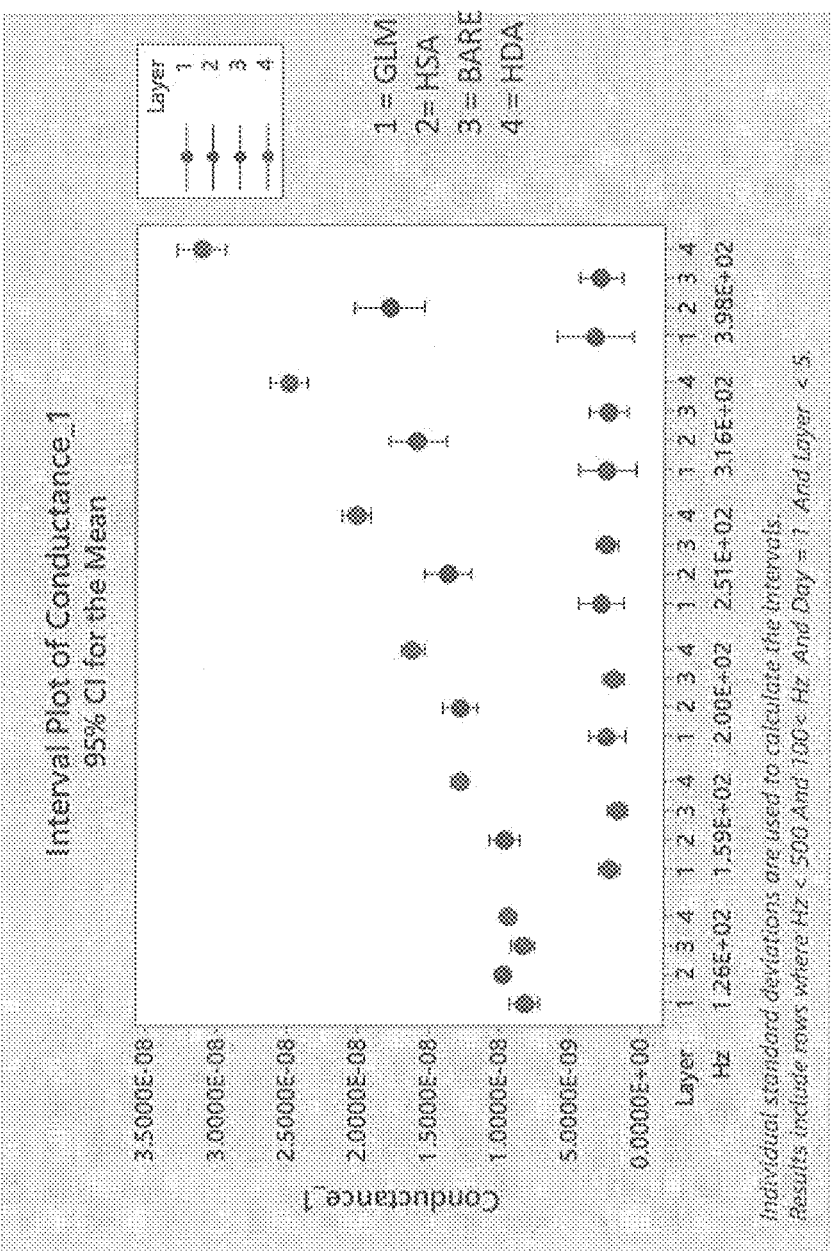
Figure 4I:
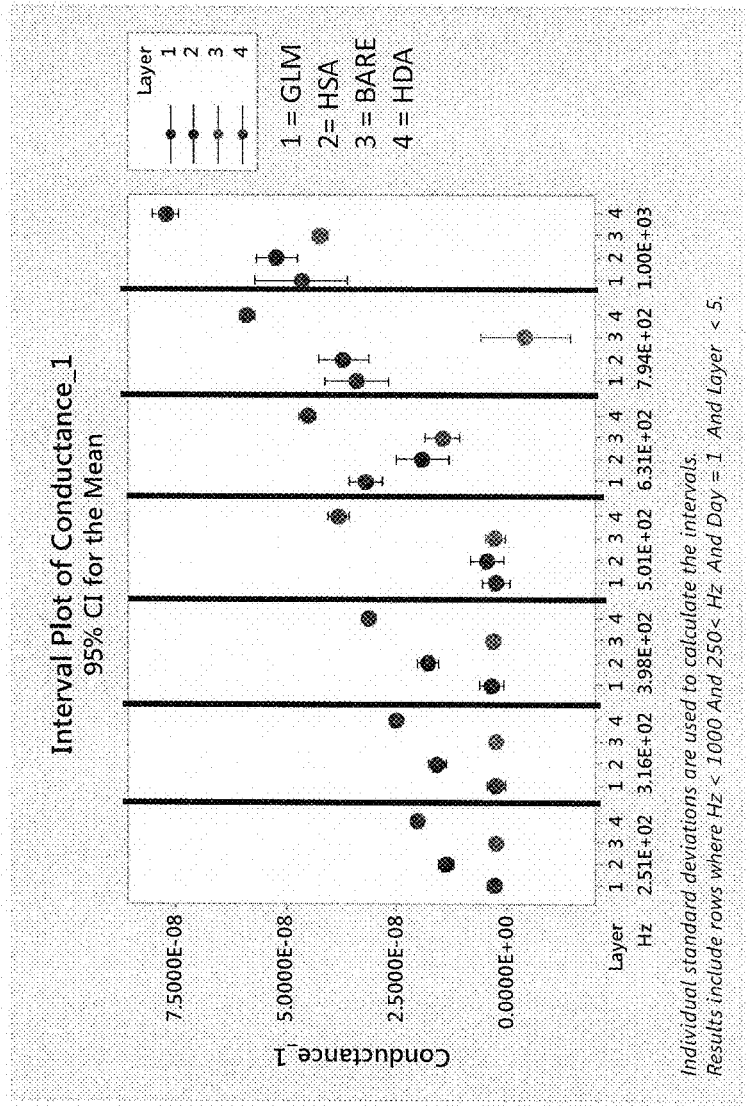

In the detailed description of the invention, references may be made to the accompanying drawings which form a part hereof, and in which is shown by way of illustration specific embodiments in which the invention may be practiced. It is to be understood that other embodiments may be utilized, and structural changes may be made without departing from the scope of the present invention. A number of different publications are also referenced herein as indicated throughout the specification. These and all publications, patents, and patent applications cited herein are hereby incorporated by reference in their entirety for all purposes.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are generally well understood and commonly employed using conventional methodology by those skilled in the art.

The inventions herein are described below with reference to flowchart illustrations of methods, systems, devices, apparatus, and programming and computer program products (see, e.g. the Figures). It will be understood that each block of the flowchart illustrations, and combinations of blocks in the flowchart illustrations, can be implemented by programing instructions, including computer program instructions (as can any menu screens described in the figures). These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein. Programming instructions may also be stored in and/or implemented via electronic circuitry, including integrated circuits (ICs) and Application Specific Integrated Circuits (ASICs) used in conjunction with sensor devices, apparatuses, and systems.

Embodiments of the invention disclosed herein provide non-Faradaic Electrochemical Impedance Spectroscopy (EIS) methods and materials for examining elements (e.g. material layers) found in devices such as sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

Illustrative Aspects and Embodiments of the Invention and Associated Materials and Methods Biomolecule sensors such as continuous glucose monitoring (CGM) sensors include enzyme based electrochemical biosensors that consist of multiple electrochemical electrodes which measure a chemical substrate via relation of electricity and chemical change. In CGM sensors, each glucose sensor consists of various layers, with electrodes on one layer which provide the interchange between patient and sensor. Each electrode contains multiple layers including but not limited to a base layer formed from materials such as polyimide, a metal layer formed from materials such as Cr and Au, an enzyme layer formed from materials such as glucose oxidase (GOx), layers that contain proteins such as human serum albumin, layers that contain adhesion promoting materials, and analyte modulating layers that modulate the diffusion of glucose therethrough. In such sensors, each layer has a target thickness for optimal functioning. The invention disclosed herein provides a reliable and effective method to measure various properties including the thickness of these material layers. By measuring the thickness of each material layer on each electrode, manufacturing quality parameters of the sensor can be observed.

The invention disclosure herein has a number of embodiments. Embodiments of the invention include methods of observing a property of a layer of a material disposed in a device comprising a first electrode electronically coupled to second electrode where the material layer is disposed over the first electrode and the second electrode. These methods comprise applying a voltage potential to the first electrode in a frequency sweep mode; and then measuring an output current that results from the application of the voltage potential. These methods then comprise using the measured output current to observe impedance characteristics of the material layer disposed over the first electrode and the second electrode; and then correlating the impedance characteristics with the property of the layer of material. In certain embodiments of the invention, output current is measured continuously during this step of the methodology.

These methods can be used to observe a variety of different properties of layer(s) of a material disposed in an electrochemical analyte sensor including, for example, the thickness of the material layer (e.g. to observe layers between 0.5 and 20 microns in thickness), the conductivity of the material layer, the architecture or roughness of the material layer, the concentration of one or more components in a composition that forms the material layer (e.g. water or glucose oxidase), or the homogeneity of a composition that forms the material layer.

Figure 5E:
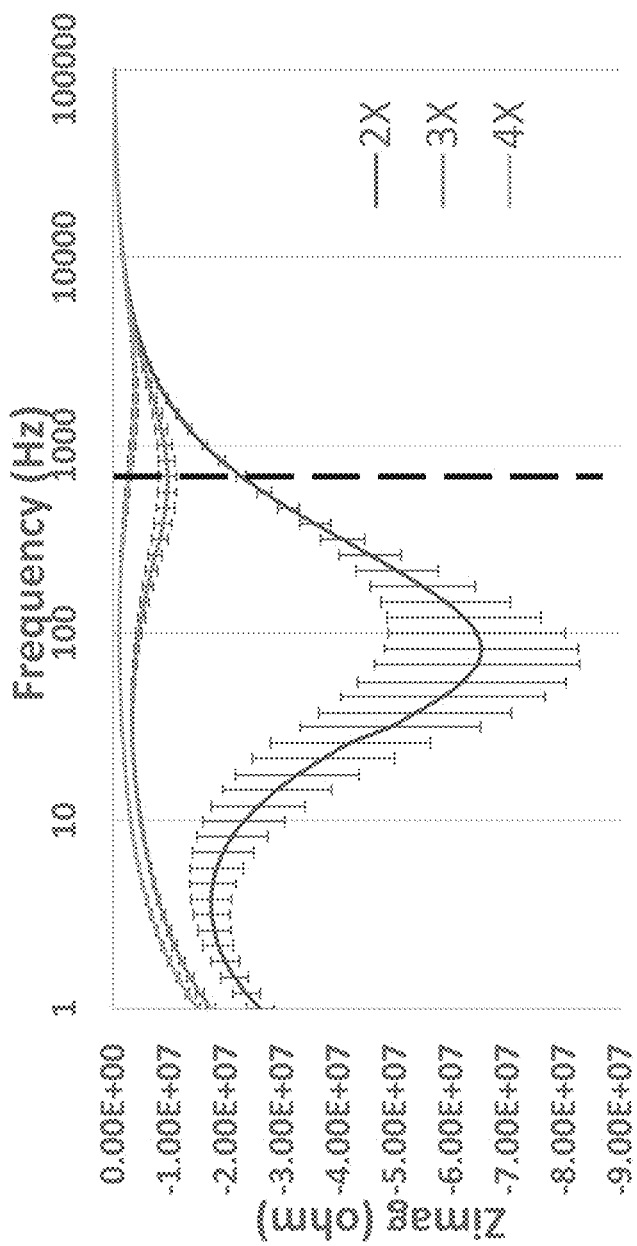
Figure 5G:
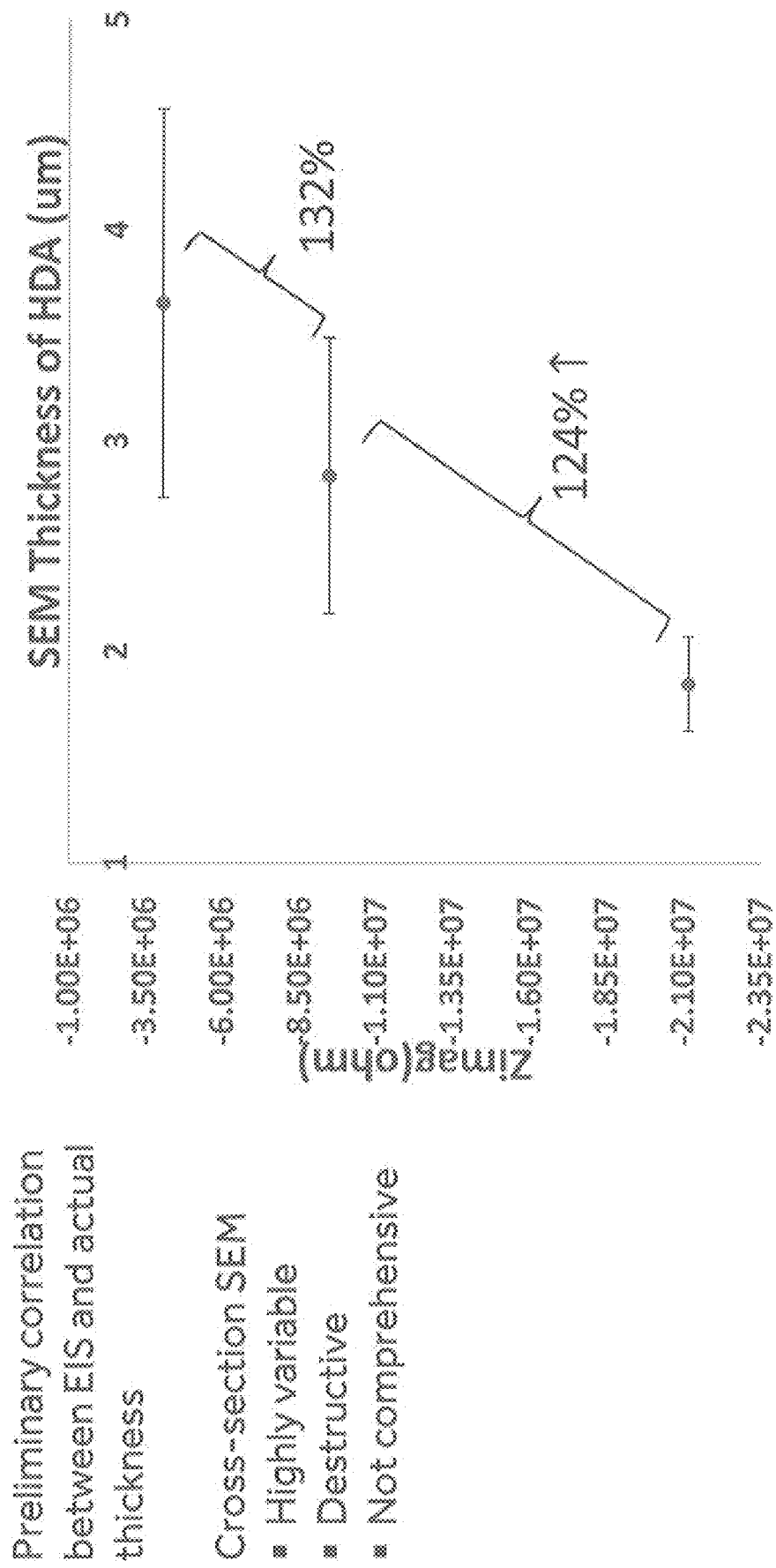

Embodiments of the invention are designed to work quickly, with the method being performed in less than 60, 30 or 20 minutes. In certain embodiments of the invention, the frequency sweep used in the method is in a range from 0.1 to 1 megahertz (or from 1 Hz to 50 Hz, 10 Hz to 100 Hz, 10 Hz to 20 Hz, 100 Hz to 3,000 Hz, 9 Hz to 11 Hz, 1000 to 3,000 Hz, or 10,000 Hz to 30,000 Hz etc.); and/or the voltage potential is between 5 volts and −5 volts (e.g. 0 volts DC, and 50 millivolts AC). Typically, the methods include correlating the impedance characteristics with the properties of the layer of material comprises application of a mathematical model of impedance and/or correlating the impedance characteristics with empirically derived data from the sample/material being tested (see e.g., the data relating to high density amine layers presented in FIG. 5G). In certain embodiment of this method no electrolyte or buffer is used, and therefore no ion is transferred between each electrode. In such embodiments, the impedance is solely based on the charge transfer within the material.

An illustrative embodiment of the invention is a method of observing a thickness of a layer of a material disposed on a glucose sensor comprising a first electrode electronically coupled to second electrode. This method comprises applying a fixed alternating current voltage in a frequency sweep mode is applied to the first electrode in a sensor architecture where the material layer is disposed over the first electrode and the second electrode; and the alternating current voltage. The method further comprises measuring an output current that results from the application of the alternating current voltage, and then using the output current measured observe or infer impedance characteristics of the material layer disposed over the first electrode and the second electrode. A final step in this method comprises correlating the impedance characteristics with the thickness of the layer of material (e.g. empirically via testing, and/or via application of a mathematical model of impedance).

The methods of the invention can be used to observe the material properties one or more layers of material found in a device, such as those found in electrochemical glucose sensors comprising 1, 2, 3, 4 or more working electrodes. As discussed in detail below, such layers include for example base layers (e.g. sensor support layers formed from a polyimide), conductive layers (e.g. those comprising one or more electrical elements such as electrodes), analyte sensing layer (e.g. those comprising an enzyme such as glucose oxidase), protein layers (e.g. those comprising polypeptides such as human serum albumin), adhesion promoting layers (e.g. those comprising a material that facilitates layer adherence such as a silane compound) and analyte modulating layer (e.g. a glucose limiting membrane that selectively limits the diffusion or glucose therethrough but not the diffusion of $O_2$ therethrough). In certain embodiments of the invention, the material layer studied is between 0.25 and 20 microns in thickness.

Typically in these methods, the thickness or other property of a plurality of layers is observed, and a specific frequency sweep mode profile is selected for the specific layer whose thickness or other property is being observed. Optionally, a plurality of properties of one or more material layers in a device such as a glucose sensor are observed using the invention disclosed herein, for example the thickness of the material layer, and in addition, the conductivity of the material layer, architecture or roughness of the material layer, concentration of a component in a composition that forms the material layer, or homogeneity of a composition that forms the material layer. In this context, embodiments of the invention can be used to observe a wide variety of device properties including but not limited to observations that provide information on the electrode-electrolyte interfaces (e.g. at an electrical double layer or a diffusion layer), or observations that provide information on the reaction mechanisms (e.g. electrochemical reactions involving the enzyme glucose oxidase), or observations that provide information on the corrosion of one or more layers, or observations that provide information on the electrodeposition on one or more layers, or observations of one or more of the material properties of the glucose sensor layers/elements described below. Moreover, while sensors are described herein as the typical devices on which the methods are practiced, these methods can be used to characterize a wide variety of other devices and the like including batteries and fuel cells.

Certain embodiments of the invention comprise dry EIS methods, and optionally include controlling the humidity of the environment under which the EIS procedure is performed. The results of such dry EIS methods are unexpected in view of what is conventionally known in this art (see, e.g. Müller et al., Sensors 2019, 19, 171; doi:10.3390/s19010171; and Hall et al., Review of Scientific Instruments 90, 015005 (2019)). As shown in FIGS. 8A-8E, there is a correlation between dry EIS function and humidity. In this context, some embodiments of the invention are designed to be performed at a selected relative humidity (RH), for example a RH that is greater than about 35% (e.g. practiced in an environment having between about 35%-55% RH). In addition, in certain embodiments of the invention, data obtained by the EIS method is evaluated by observing Zimag (ohms). In other embodiments of the invention, data is evaluated by observing Zphase (degree). In typical embodiments of the invention, Zphase is preferred over Zimag. Optionally, data is evaluated by observing Zphase and this data is then evaluated using a humidity normalization algorithm.

As disclosed herein, Electrochemical Impedance Spectroscopy (EIS) procedure are used to observe impedance-related parameters for one or more sensing electrodes. The parameters may include real impedance, imaginary impedance, impedance magnitude, and/or phase angle. The observed values of the impedance-related parameters are then used to obtain information on one or more layers of material disposed over an electrode. Advantageously, impedance-related parameters can be designed to be specific for a material layer of interest. Electrochemical Impedance Spectroscopy (EIS) methods that can be adapted for use with embodiments of the invention are well known in the art (e.g. U.S. Patent Publication Nos. 20150300969, 20130331676, 20110230741, 20080000779 and 20070170073, and International Publication Number WO 2013/184416). In this context, the general relation between the potential and the current (which is directly related with the amount of electrons and so the charge transfer via Faradays law) is:

$$i = i_0\left(\frac{C_O}{C^*_O}\exp\left(\frac{\alpha nF\eta}{RT}\right) - \left(\frac{C_R}{C^*_R}\exp\left(\frac{-(1-\alpha)nF\eta}{RT}\right)\right)\right)$$

$I_0$=exchange current density
$C_O$=concentration of oxidant at the electrode surface
$C_O^*$=concentration of oxidant in the bulk
$C_R$=concentration of reductant at the electrode surface
η=overpotential
F=Faradays constant
T=temperature
R=gas constant
A=reaction order
N=number of electrons involved When the overpotential, η, is very small and the electrochemical system is at equilibrium, the expression for the charge-transfer resistance changes to $$R_{ct} = \frac{RT}{nFi_0}$$

From this equation the exchange current density can be calculated when $R_{ct}$ is known. As disclosed herein, such conventional EIS phenomena can be adapted to measure the material properties of one or more layers of material in a device such as an amperometric glucose sensor.

In typical glucose sensor embodiments of the invention, electrochemical glucose sensors are operatively coupled to a sensor input capable of receiving signals from the electrochemical sensor; and a processor coupled to the sensor input, wherein the processor is capable of characterizing one or more signals received from the electrochemical sensor. In certain embodiments of the invention, the electrical conduit of the electrode is coupled to a potentiostat. In certain embodiments of the invention, the processor is capable of comparing a first signal received from a working electrode in response to a first working potential with a second signal received from a working electrode in response to a second working potential. Optionally, the electrode is coupled to a processor adapted to convert data obtained from observing fluctuations in electrical current from a first format into a second format. Such embodiments include, for example, processors designed to convert a sensor current Input Signal (e.g. ISIG measured in nA) to a blood glucose concentration.

In some embodiments of the invention, the apparatus comprises a plurality of working electrodes, counter electrodes and reference electrodes, for example in an architecture where they are clustered together in units consisting essentially of one working electrode, one counter electrode and one reference electrode; and the clustered units are longitudinally distributed on the base layer in a repeating pattern of units. In some sensor embodiments, the distributed electrodes are organized/disposed within a flex-circuit assembly (i.e. a circuitry assembly that utilizes flexible rather than rigid materials). Such flex-circuit assembly embodiments provide an interconnected assembly of elements (e.g. electrodes, electrical conduits, contact pads and the like) configured to facilitate wearer comfort (for example by reducing pad stiffness and wearer discomfort).

In some embodiments of the invention, an analyte sensing layer is disposed over electrically conductive members, and includes an agent that is selected for its ability to detectably alter the electrical current at the working electrode in the presence of an analyte. In the working embodiments of the invention that are disclosed herein, the agent is glucose oxidase, a protein that undergoes a chemical reaction in the presence of glucose that results in an alteration in the electrical current at the working electrode. These working embodiments further include an analyte modulating layer disposed over the analyte sensing layer, wherein the analyte modulating layer modulates the diffusion of glucose as it migrates from an in vivo environment to the analyte sensing layer. In certain embodiments of the invention, the analyte modulating layer comprises a hydrophilic comb-copolymer having a central chain and a plurality of side chains coupled to the central chain, wherein at least one side chain comprises a silicone moiety. In certain embodiments of the invention, the analyte modulating layer comprises a blended mixture of: a linear polyurethane/polyurea polymer, and a branched acrylate polymer. In working embodiments of the present invention, the signal strength and $O_2$ response of the microarray sensor electrode can be increased with the use of a 2× permselective GLM (glucose limiting membrane). Typically, this analyte modulating layer composition comprises a first polymer formed from a mixture comprising a diisocyanate; at least one hydrophilic diol or hydrophilic diamine; and a siloxane; that is blended with a second polymer formed from a mixture comprising: a 2-(dimethyl-amino)ethyl methacrylate; a methyl methacrylate; a polydimethyl siloxane monomethacryloxypropyl; a poly(ethylene oxide) methyl ether methacrylate; and a 2-hydroxyethyl methacrylate. Additional material layers can be included in such apparatuses. For example, in some embodiments of the invention, the apparatus comprises an adhesion promoting layer disposed between the analyte sensing layer and the analyte modulating layer.

Figure 6:
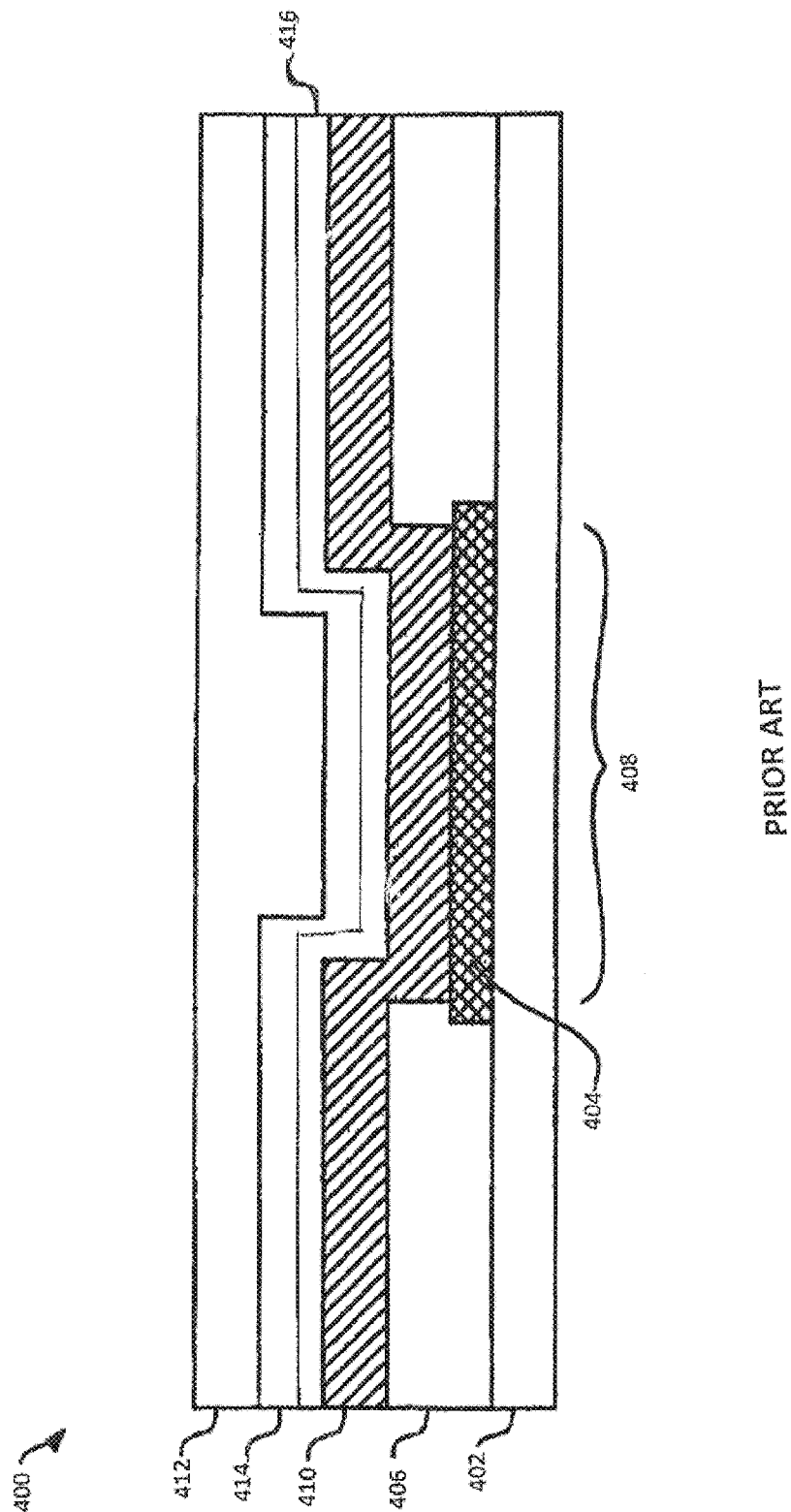
FIG. 6 shows a sensor design comprising an amperometric analyte sensor formed from a plurality of planar layered elements.

One sensor embodiment shown in FIG. 6 is an amperometric sensor 400 having a plurality of layered elements including a base layer 402 (e.g. one formed from a polymer disclosed herein), a conductive layer 404 (e.g. one comprising the plurality of electrically conductive members) which is disposed on and/or combined with the base layer 402. Typically, the conductive layer 404 comprises one or more electrodes. An analyte sensing layer 410 (typically comprising an enzyme such as glucose oxidase) can be disposed on one or more of the exposed electrodes of the conductive layer 404. A protein layer 416 can be disposed upon the analyte sensing layer 410. An analyte modulating layer 412 can be disposed above the analyte sensing layer 410 to regulate analyte (e.g. glucose) access with the analyte sensing layer 410. An adhesion promoter layer 414 is disposed between layers such as the analyte modulating layer 412 and the analyte sensing layer 410 as shown in FIG. 6 in order to facilitate their contact and/or adhesion. This embodiment also comprises a cover layer 406 such as a polymer surface coating disclosed herein can be disposed on portions of the sensor 400. Apertures 408 can be formed in one or more layers of such sensors. Amperometric glucose sensors having this type of design are disclosed, for example, in U.S. Patent Application Publication Nos. 20070227907, 20100025238, 20110319734 and 20110152654, the contents of each of which are incorporated herein by reference.

Specific aspects of embodiments of the invention are discussed in detail in the following sections.

Figure 7:
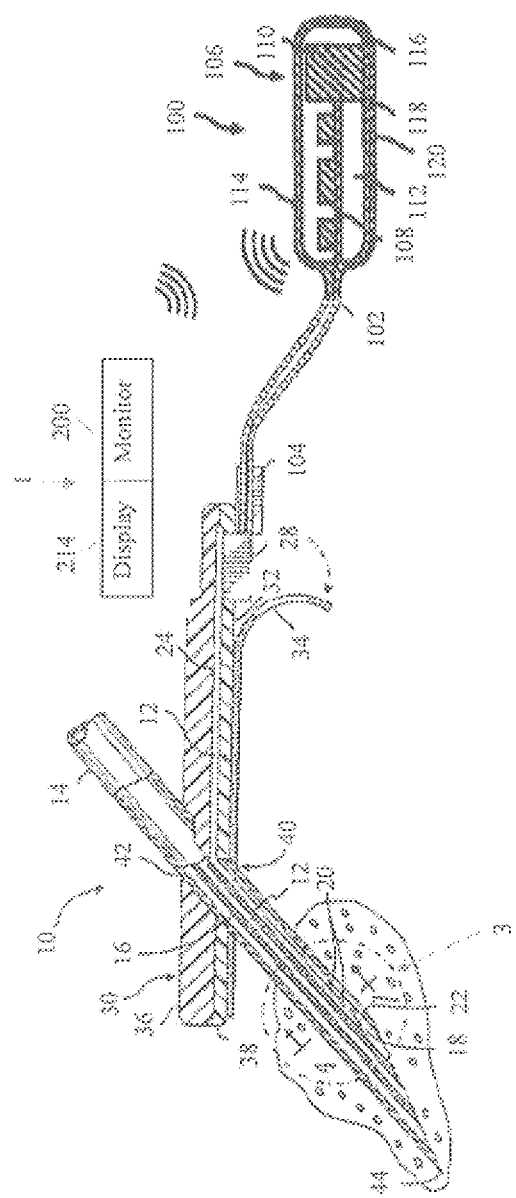
FIG. 7 provides a perspective view illustrating a subcutaneous sensor insertion set, a telemetered characteristic monitor transmitter device, and a data receiving device embodying features of the invention.
Figure 8A:
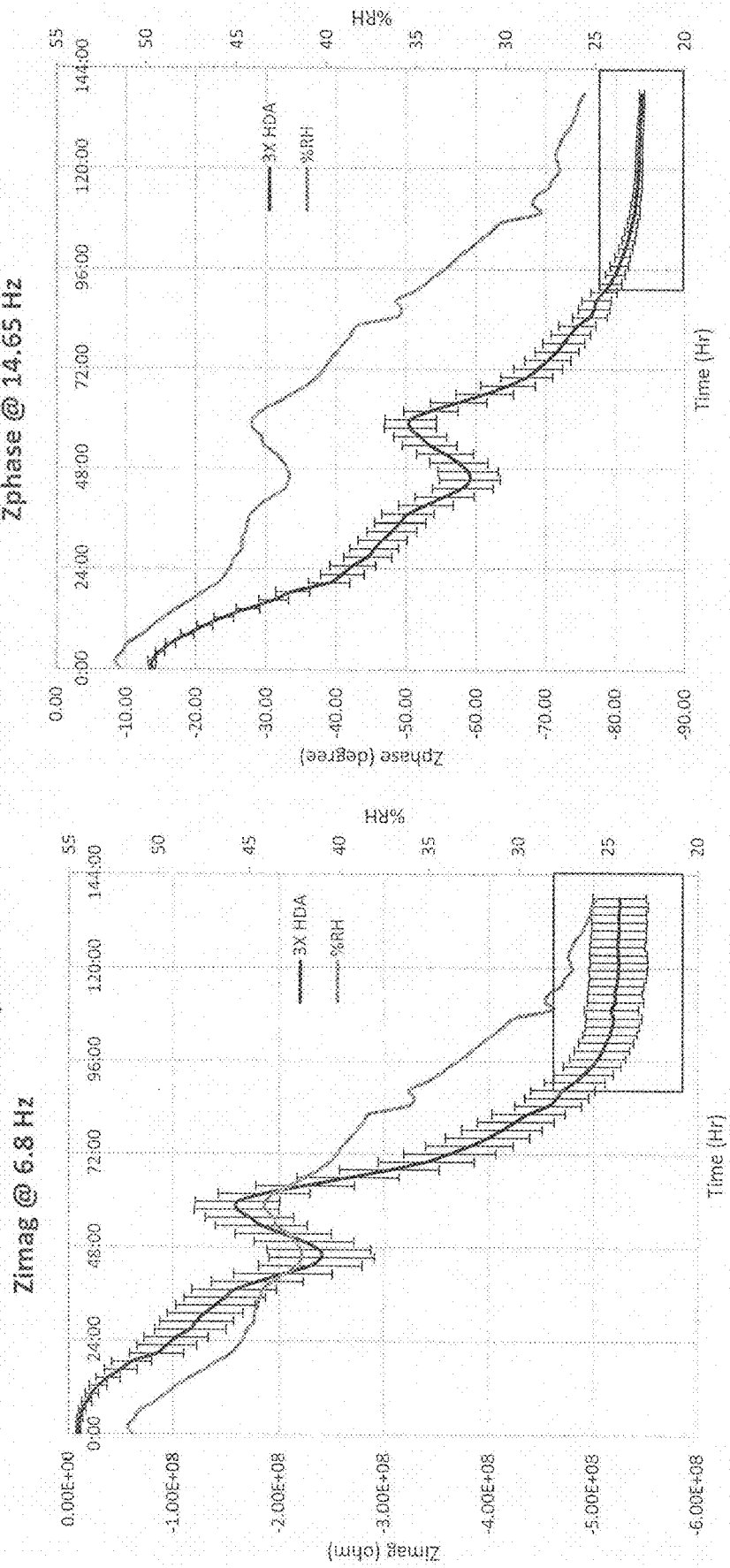
Figure 8C:
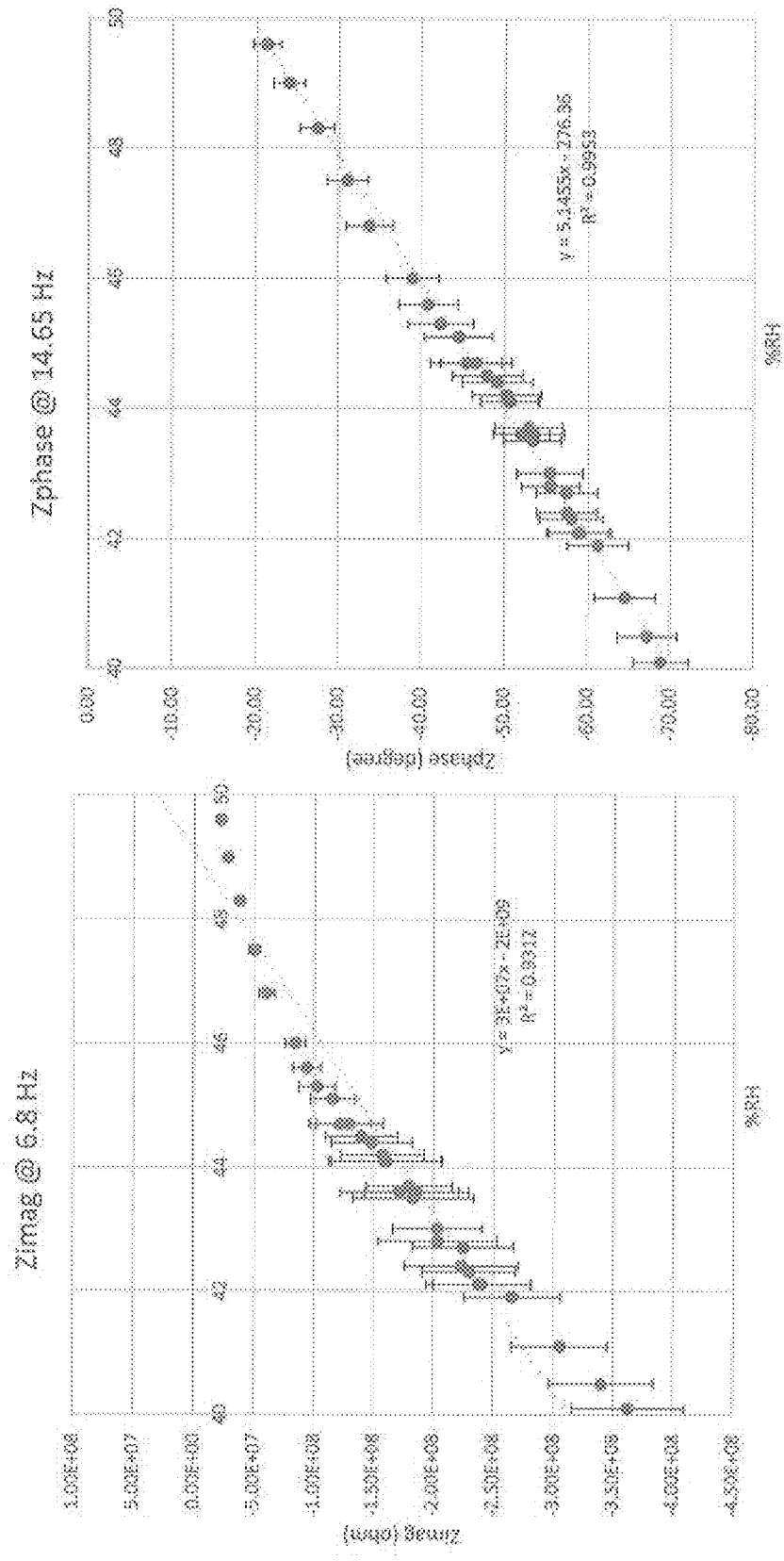

Typical Elements, Configurations and Analyte Sensor Embodiments of the Invention A. Typical Elements Found in of Embodiments of the Invention FIGS. 6 and 7 provide illustrations of various sensor and sensor system embodiments of the invention.

FIG. 6 illustrates a cross-section of a typical sensor embodiment 400 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 6. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 6 includes a base layer 402 to support the sensor 400. The base layer 402 can be made of a material such as a polymeric surface having the constellation of elements disclosed herein, a metal and/or a ceramic, which may be self-supporting or further supported by another material as is known in the art. Embodiments of the invention include a conductive layer 404 which is disposed on and/or combined with the base layer 402. Typically, the conductive layer 404 comprises one or more electrically conductive elements that function as electrodes. An operating sensor 400 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 402 and/or conductive layer 404 can be generated using many known techniques and materials. In certain embodiments of the invention, the electrical circuit of the sensor is defined by etching the disposed conductive layer 404 into a desired pattern of conductive paths. A typical electrical circuit for the sensor 400 comprises two or more adjacent conductive paths with regions at a proximal end to form contact pads and regions at a distal end to form sensor electrodes. An electrically insulating cover layer 406 such as a polymer coating can be disposed on portions of the sensor 400. Acceptable polymer coatings for use as the insulating protective cover layer 406 can include, but are not limited to polymers having the constellation of features disclosed herein, non-toxic biocompatible polymers such as silicone compounds, polyimides, biocompatible solder masks, epoxy acrylate copolymers, or the like. In the sensors of the present invention, one or more exposed regions or apertures 408 can be made through the cover layer 106 406 to open the conductive layer 404 to the external environment and to, for example, allow an analyte such as glucose to permeate the layers of the sensor and be sensed by the sensing elements. Apertures 408 can be formed by a number of techniques, including laser ablation, tape masking, chemical milling or etching or photolithographic development or the like. In certain embodiments of the invention, during manufacture, a secondary photoresist can also be applied to the protective layer 406 to define the regions of the protective layer to be removed to form the aperture(s) 408. The exposed electrodes and/or contact pads can also undergo secondary processing (e.g. through the apertures 408), such as additional plating processing, to prepare the surfaces and/or strengthen the conductive regions.

In the sensor configuration shown in FIG. 6, an analyte sensing layer 410 is disposed on one or more of the exposed electrodes of the conductive layer 404. Typically, the analyte sensing layer 410 is an enzyme layer. Most typically, the analyte sensing layer 410 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 410 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current.

In embodiments of the invention, the analyte sensing layer 410 can be applied over portions of the conductive layer or over the entire region of the conductive layer. Typically, the analyte sensing layer 410 is disposed on the working electrode which can be the anode or the cathode. Optionally, the analyte sensing layer 410 is also disposed on a counter and/or reference electrode. Methods for generating a thin analyte sensing layer 410 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 410 is coated and or disposed next to one or more additional layers. Optionally, the one or more additional layers includes a protein layer 416 disposed upon the analyte sensing layer 410. Typically, the protein layer 416 comprises a protein such as human serum albumin, bovine serum albumin or the like. Typically, the protein layer 416 comprises human serum albumin. In some embodiments of the invention, an additional layer includes an analyte modulating layer 412 that is disposed above the analyte sensing layer 410 to regulate analyte contact with the analyte sensing layer 410. For example, the analyte modulating membrane layer 412 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, an adhesion promoter layer 414 is disposed between the analyte modulating layer 412 and the analyte sensing layer 410 as shown in FIG. 6 in order to facilitate their contact and/or adhesion. In a specific embodiment of the invention, an adhesion promoter layer 414 is disposed between the analyte modulating layer 412 and the protein layer 416 as shown in FIG. 6 in order to facilitate their contact and/or adhesion. The adhesion promoter layer 414 can be made from any one of a wide variety of materials known in the art to facilitate the bonding between such layers. Typically, the adhesion promoter layer 414 comprises a silane compound. In alternative embodiments, protein or like molecules in the analyte sensing layer 410 can be sufficiently crosslinked or otherwise prepared to allow the analyte modulating membrane layer 412 to be disposed in direct contact with the analyte sensing layer 410 in the absence of an adhesion promoter layer 414.

B. Typical Analyte Sensor Layer/Constituents Observed in Embodiments of the Invention The following disclosure provides examples of typical layers/constituents that can be observed by EIS in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 402 in FIG. 6). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material such as a polymer comprising a surface having the constellation of features disclosed herein that function to modulate immune response. This base constituent can be made of a wide variety of materials having desirable qualities such as the constellation of features disclosed herein as well as dielectric properties, water impermeability and hermeticity.

Some materials include metallic, and/or ceramic and/or polymeric substrates or the like.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 404 in FIG. 6). The term "conductive constituent" is used herein according to art accepted terminology and refers to electrically conductive sensor elements such as a plurality of electrically conductive members disposed on the base layer in an array (e.g. so as to form a microarray electrode) and which are capable of measuring a detectable signal and conducting this to a detection apparatus. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 410 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1× reference electrode, a 2.6× working electrode and a 3.6× counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the electrodes of the sensor (see, e.g. element 410 in FIG. 6). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 416 in FIG. 6). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 414 in FIG. 6). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

Analyte Modulating Constituent

The electrochemical sensors of the invention include an analyte modulating constituent disposed on the sensor (see, e.g. element 412 in FIG. 6). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

High-Density Amine Constituent

The electrochemical sensors of the invention can include one or more high-density amine constituent layers that provide the sensors with a number of beneficial functions. Such layers can optimize sensor function, for example by acting as an adhesion promoting constituent for layers adjacent to the HDA layer, by decreasing fluctuations that can occur in glucose oxidase based sensors in the presence of fluctuating concentration of oxygen, by improving sensor initialization profiles and the like. The term "adhesion promoting constituent" is used herein according to art accepted terminology and refers to a constituent that includes materials selected for their ability to promote adhesion between adjoining constituents in the sensor. Typically, the high-density amine adhesion promoting constituent is disposed between and in direct contact with the analyte sensing constituent and the analyte modulating constituent. In typical embodiments, the high-density amine layer 500 comprises poly-1-lysine having molecular weights between 30 KDa and 300 KDa (e.g. between 150 KDa and 300 KDa). The concentrations of poly-1-lysine in such high-density amine layers 500 is typically from 0.1 weight-to-weight percent to 0.5 weight-to-weight percent and the high-density amine layer 500 is from 0.1 to 0.4 microns thick. In embodiments where the analyte sensing layer comprises glucose oxidase so that the analyte sensor senses glucose, and the high-density amine layer 500 functions to decrease sensor signal changes that result from fluctuating levels of oxygen ($O_2$).

Cover Constituent

The electrochemical sensors of the invention include one or more cover constituents which are typically electrically insulating protective constituents (see, e.g. element 406 in FIG. 6). Typically, such cover constituents can be in the form of a coating, sheath or tube and are disposed on at least a portion of the analyte modulating constituent. Typically, such features comprise a polymer comprising a surface having the constellation of features disclosed herein that function to modulate immune response. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Typical Analyte Sensor Systems Used in Embodiments of the Invention FIG. 11 in U.S. Patent Publication 2014/0163346 shows a schematic of a potentiostat that may be used to measure current in embodiments of the present invention. As shown in FIG. 11 in U.S. Patent Publication 2014/0163346, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

Embodiments of the invention include devices which process display data from measurements of a sensed material layer characteristic (e.g. thickness) in a manner and format tailored to allow a user of the device to easily monitor the status of that characteristic. An illustrative embodiment of the invention is a device comprising a input capable of receiving a signal from a device such as a glucose sensor, the signal being based on a sensed material layer characteristic value of a device; a memory for storing a plurality of measurements of the sensed material layer characteristic value of the device from the received signal from the sensor; and a display for presenting a text and/or graphical representation of the plurality of measurements of the sensed material layer characteristic value (e.g. text, a line graph or the like, a bar graph or the like, a grid pattern or the like or a combination thereof).

FIG. 7 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 7 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 100 by a connector block 28 (or the like).

As shown in FIG. 7, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 100 is coupled to a sensor set 10 by a cable 102 through a connector 104 that is electrically coupled to the connector block 28 of the connector portion 24 of the sensor set 10.

In the embodiment shown in FIG. 7, the telemetered characteristic monitor 100 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use.

In the illustrative embodiment shown in FIG. 7, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. Nos.

4,562,751; 4,678,408; 4,685,903 or 4,573,994, to control delivery of insulin to a diabetic patient.

In the illustrative embodiment shown in FIG. 7, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 7, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 102 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

What is claimed is:

1. A method of observing a property of a layer of a material disposed on an analyte sensor comprising a first electrode electronically coupled to second electrode; the method comprising:
    (a) applying a voltage potential to the first electrode, wherein:
        the material layer is disposed over the first electrode and the second electrode;
        and the voltage potential is applied in a frequency sweep mode;
    (b) measuring an output current that results from the application of the voltage potential;
    (c) using the measurement from (b) to observe impedance characteristics of the material layer disposed over the first electrode and the second electrode; and
    (d) correlating the impedance characteristics with the property of the layer of material;
wherein correlating the impedance characteristics with the properties of the layer of material comprises application of a mathematical model of impedance.

2. The method of claim 1, wherein a property comprises:
    a conductivity of the material layer;
    a thickness of the material layer;
    an architecture or roughness of the material layer;
    a concentration of a component in a composition that forms the material layer; or
    homogeneity of a composition that forms the material layer.

3. The method of claim 1, wherein the frequency sweep is in a range from 0.1 to 1 megahertz.

4. The method of claim 1, wherein the voltage potential is between 5 volts and −5 volts.

5. The method of claim 1, wherein the method is performed in less than 60, 30 or 20 minutes.

6. An electrochemical impedance spectroscopy (EIS) method of observing a thickness of a layer of a material disposed on a glucose sensor comprising a first electrode electronically coupled to second electrode; the method comprising:
    (a) applying a fixed voltage to the first electrode, wherein:
        the material layer is disposed over the first electrode and the second electrode;
        and an alternating current voltage is applied in a frequency sweep mode;
    (b) measuring an output current that results from the application of the voltage;
    (c) using the measurement from (b) to observe impedance characteristics of the material layer disposed over the first electrode and the second electrode; and
    (d) correlating the impedance characteristics with the thickness of the layer of material.

7. The method of claim 6, wherein the material layer is between 0.5 and 20 microns in thickness.

8. The method of claim 6, wherein the glucose sensor comprises at least one of:
    a base layer;
    a conductive layer;
    an analyte sensing layer;
    a protein layer;
    an adhesion promoting layer;
    a high density amine layer; and
    an analyte modulating layer.

9. The method of claim 8, wherein a frequency sweep mode profile is selected for the layer whose thickness is being observed.

10. The method of claim 9, where the layer is the analyte sensing layer.

11. The method of claim 9, where the layer is the high density amine layer.

12. The method of claim 9, wherein the thickness of a plurality of layers is observed.

13. The method of claim 6, further comprising using the method to observe a second property of a material layer in the glucose sensor.

14. The method of claim 13, wherein a property comprises:
    a conductivity of the material layer;
    an architecture or roughness of the material layer;
    a concentration of a component in a composition that forms the material layer; or
    homogeneity of a composition that forms the material layer.

15. The method of claim 6, wherein the glucose sensor comprises 2, 3, 4 or more working electrodes.

16. A method of observing a property of a layer of a material disposed on an analyte sensor comprising a first electrode electronically coupled to second electrode; the method comprising:
   (a) applying a voltage potential to the first electrode, wherein:
      the material layer is disposed over the first electrode and the second electrode;
      and the voltage potential is applied in a frequency sweep mode;
   (b) measuring an output current that results from the application of the voltage potential;
   (c) using the measurement from (b) to observe impedance characteristics of the material layer disposed over the first electrode and the second electrode; and
   (d) correlating the impedance characteristics with the property of the layer of material;
wherein no ions are transferred between the first electrode and the second electrode in the method such that impedance measured is solely based on charge transfer within the layer of material.

17. A method of observing a property of a layer of a material disposed on an analyte sensor comprising a first electrode electronically coupled to second electrode; the method comprising:
   (a) applying a voltage potential to the first electrode, wherein:
      the material layer is disposed over the first electrode and the second electrode;
      and the voltage potential is applied in a frequency sweep mode;
   (b) measuring an output current that results from the application of the voltage potential;
   (c) using the measurement from (b) to observe impedance characteristics of the material layer disposed over the first electrode and the second electrode; and
   (d) correlating the impedance characteristics with the property of the layer of material;
wherein the property comprises a thickness of the material layer, and the thickness is between 0.5 and 20 microns.

18. A method of observing a property of a layer of a material disposed on an analyte sensor comprising a first electrode electronically coupled to second electrode; the method comprising:
   (a) applying a voltage potential to the first electrode, wherein:
      the material layer is disposed over the first electrode and the second electrode;
      and the voltage potential is applied in a frequency sweep mode;
   (b) measuring an output current that results from the application of the voltage potential;
   (c) using the measurement from (b) to observe impedance characteristics of the material layer disposed over the first electrode and the second electrode; and
   (d) correlating the impedance characteristics with the property of the layer of material;
wherein output current is measured continuously in step (b).

* * * * *